US008758653B2

(12) United States Patent
Chmelka et al.

(10) Patent No.: US 8,758,653 B2
(45) Date of Patent: Jun. 24, 2014

(54) MOLECULAR OPTIMIZATION OF MULTIPLY-FUNCTIONALIZED MESOSTRUCTURED MATERIALS

(75) Inventors: Bradley F. Chmelka, Goleta, CA (US);
George L. Athens, Midland, MI (US);
Robert Messinger, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 379 days.

(21) Appl. No.: 12/792,590

(22) Filed: Jun. 2, 2010

(65) Prior Publication Data

US 2010/0311856 A1 Dec. 9, 2010

Related U.S. Application Data

(60) Provisional application No. 61/183,485, filed on Jun. 2, 2009.

(51) Int. Cl.
*B05D 5/12* (2006.01)
*B82Y 30/00* (2011.01)
*B82Y 40/00* (2011.01)

(52) U.S. Cl.
USPC ............... 252/519.4; 252/519.51; 427/126.1

(58) Field of Classification Search
CPC .......... B82Y 30/00; B82Y 40/00; C01G 1/12; B05D 5/12; B01J 29/0308; B01J 35/10; C01P 2006/40
USPC ............. 516/99, 100, 110–112; 502/158; 252/519.4, 519.51; 257/E21.582; 438/95, 103; 427/126.1
See application file for complete search history.

(56) References Cited

U.S. PATENT DOCUMENTS

| | | | | |
|---|---|---|---|---|
| 6,326,326 | B1 * | 12/2001 | Feng et al. | 502/62 |
| 8,226,740 | B2 * | 7/2012 | Chaumonnot et al. | 75/252 |
| 2004/0217061 | A1 * | 11/2004 | Corzani et al. | 210/660 |
| 2007/0131609 | A1 * | 6/2007 | Ramaswamy et al. | 210/490 |
| 2007/0191499 | A1 * | 8/2007 | Chmelka et al. | 521/27 |

OTHER PUBLICATIONS

Gerstein, B.C. et al.—"High-Resolution n.m.r. in Solids with Strong Homonuclear Dipolar Broadening: Combined Multiple-Pulse Decoupling and Magic Angle Spinning (and Discussion)"—Phil. Trans. R. Soc. Lond. A, vol. 299, 1981, pp. 521-546.
Zeidan, R.K. et al.—"Multifunctional Heterogeneous Catalysts: SBA-15-Containing Primary Amines and Sulfonic Acids"—Angew. Chem. Int. Ed., vol. 45, 2006, pp. 6332-6335.
Zhang, J. et al.—"High temperature PEM fuel cells"—Journal of Power Sources, vol. 160, 2006, pp. 872-891.
Zhao, D. et al.—"Continuous Mesoporous Silica Films with Highly Ordered Large Pore Structures"—Avd. Mater., vol. 10, 1998, p. 1380-1385.

(Continued)

*Primary Examiner* — Mark Kopec
(74) *Attorney, Agent, or Firm* — John P. O'Banion

(57) ABSTRACT

A material and method for producing mesostructured materials with multiple functionalities that are independently adjustable and collectively optimizable is provided. The method uses a series of discrete synthesis steps under otherwise mutually incompatible conditions, e.g., from acidic, alkaline, and/or non-aqueous solutions, allows different functionalities to be introduced to the materials and optimized. To illustrate the method, cubic mesoporous silica films were prepared from strongly acidic solutions that were separately functionalized under highly alkaline conditions to incorporate hydrophilic aluminosilica moieties and under non-aqueous conditions to introduce perfluorosulfonic-acid surface groups.

8 Claims, 22 Drawing Sheets

(56) References Cited

OTHER PUBLICATIONS

Zhao, D. et al.—"Synthesis of continuous mesoporous silica thin films with three-dimensional accessible pore structures"—Chem. Commun., 1998, pp. 2499-2500.

Adams, R.—"Bimetallic cluster complexes: synthesis, structures and applications to catalysts"—Jour. of Organometallic Chemistry, vol. 689, 2004, pp. 4521-4529.

Alexeev, O.S. et al.—"Supported Bimetallic Cluster Catalysts"—Ind. Eng. Chem. Res., vol. 42, 2003, p. 1571-1587.

Alvarez, F. et al.—"Hydroisomerization and Hydrocracking of Alkanes"—Journ. of Catalysts, vol. 162, 1996, article No. 0275, pp. 179-189.

Alvaro, M. et al.—""Nafion"—functionalized mesoporous MCM-41 silica shows high activity and selectivity for carboxylic acid esterification and Friedel-Crafts acylation reactions"—Journ. of Catalysts, vol. 231, 2005, pp. 48-55.

Angelome, P.C. et al.—"Organically Modified Transition-Metal Oxide Mesoporous Thin Films and Xerogels"—Chem. Matter, vol. 17, 2005, pp. 322-331.

Angelome, P.C. et al.—"Ordered mesoporous hybrid thin films with double organic functionality and mixed oxide framework"—Journ. Chem Matter, vol. 15, 2005, pp. 3903-3912.

Asefa, T. et al.—"Novel Bifunctional Periodic Mesoporous Organosilicas, BPMOs: Synthesis, Characterization, Properties and in-Situ Selective Hydroboration-Alcoholysis Reactions of Functional Groups"—Jour. Am. Chem. Soc., vol. 123, 2001, pp. 8520-8530.

Asefa, T. et al.—Periodic mesoporous organosilicas with organic groups inside the channel walls—Nature, vol. 402, issue 23, Dec. 1999, pp. 0867-0871.

Athens, G.L. et al.—"Acid-Functionalized Mesostructured Aluminosilica for Hydrophilic Proton Conduction Membranes"—Adv. Mater., col. 19, 2007, pp. 2580-2587.

Burkett, S.L. et al.—"Synthesis of hybrid inorganic-organic mesoporous silica by co-condensation of siloxane and organosiloxane precursers"—Chem. Commun, 1996, pp. 1367-1368.

Casciolo, M. et al.—"On the decay of Nafion proton conductivity at high temperature and relative humidity"—Journ. of Power Sources, vol. 162, 2006, pp. 141-145.

Che, S. et al.—"Synthesis and characterization of chiral mesoporous silica"—Nature, vol. 429, May 20, 2004, pp. 281-284.

Chin, D. et al.—"On the conductivity of phosphoric acid electrolyte"—Journ. of Applied Electrochemistry, vol. 19, 1989, pp. 95-99.

Christiansen, A.W.—"Resorcinol-formaldehyde Reactions in Dilute Solution Observed by Carbon-13, NMR Spectroscopy"—Journ. of Applied Polymer Science, vol. 75, 2000, pp. 1760-1768.

Davis, M.E. et al.—"Zeolite and Molecular Sieve Synthesis"—Chem. Mater., vol. 4, 1992, pp. 756-768.

Wight, A.P. et al.—"Design and Preparation of Organic-Inorganic Hybrid Catalysts"—Chem. Rev., vol. 102, 2002, pp. 3589-3614.

Diaz, I. et al.—"Combined Alkyl and Sulfonic Acid Functionalization of MCM-41-Type Silica"—Jour. of Catalysts, vol. 193, 2000, pp. 283-294.

Dufaud, V. et al.—"Design of Heterogeneous Catalysts via Multiple Active Site Positioning in Organic-Inorganic Hybrid Materials"—Journ. Am. Chem. Soc., vol. 125, 2003, pp. 9403-9413.

Fowler, C.E. et al.—"Covalent coupling of an organic chromophore into functionalized MCM-41 mesophases by template-directed co-condensation"—Chem, Commun., 1998, pp. 1825-1826.

Girgis, M.J. et al.—"Impact of Catalyst Metal-Acid Balance in n-Hexadecane Hydroisomerization and Hydrocracking"—Ind. Eng. Chem. Res., vol. 35, 1996, pp. 386-396.

Hall, S.R. et al.—"Template-directed synthesis of bi-functionalized organo-MCM-41 and phenyl-MCM-48 silica mesophases"—Chem. Commun., 1999, pp. 201-202.

Hoffman, F. et al.—"Silica-Based Mesoporous Organic-Inorganic Hybrid Materials"—Angewandte Chemie, vol. 45, 2006, 3216-3251.

Jannasch, P.—"Recent Developments in high-temperature proton conducting polymer electrolyte membranes"—Current Opinion in Colloid and Interface Science 9, 2003, pp. 96-102.

Kim, M.G. et al.—"Investigation of a Resorcinol-Formaldehyde Resin by 13C-NMR Spectroscopy and Intrinsic Viscosity Measurement"—Jour. of Polymer Science: Part A: Polymer Chemistry, vol. 31, 1993, pp. 1871-1877.

Kreuer, K.D.—"On the development of proton conducting polymer membranes for hydrogen and methanol fuel cells"—Journ. of Membrane Science, vol. 185, 201, pp. 29-39, 2001.

Li, Q. et al.—"Approaches and Recent Development of Polymer Electrolyte Membranes for Fuel Cells Operating above 100C"—Chem Mater. vol. 15, 2003, pp. 4896-4915.

Lim, M.H. et al.—"Synthesis and Characterization of a Reactive Vinyl-Functionalized MCM-41: Probing the Internal Pore Structure by a Bromination Reaction"—Journ. Am. Chem. Soc., vol. 119, 1997, pp. 4090-4091.

Liu, C. et al.—"Facile synthesis of ordered mesoporous carbons from F108/resorcinol-formaldehyde composites obtained in the basic media"—Chem. Commun., 2007, pp. 757-759.

Liu, R. et al.—"Triconstituent Co-assembly to Ordered Mesostructured Polymer-Silica and Carbon-Silica Nanocomposites and Large-Pore Mesoporous Carbons with High Surface Areas"—Journ. Am. Chem. Soc, vol. 128, 2006, pp. 11652-11662.

Luan, Z. et al.—"Alumination and Ion Exchange of Mesoporous SBA-15 Molecular Sieves"—Chem. Mater., vol. 11, 1999, pp. 1621-1627.

Macquarrie, D.J.—"Direct preparation of organically modified MCM-type materials. Preparation and characterisation of aminopropyl-MCM and 2-cyanoethyl-MCM"—Chem. Commun., 1996, pp. 1961-1962.

Margolese, D. et al.—"Direct Synthesis of Ordered SBA-15 Mesoporous Silica Containing Sulfonic Acid Groups"—Chem. Mater., vol. 12, 2000, pp. 2448-2459.

Melero, J.A. et al.—"Advances in the Synthesis and Catalytic Applications of Organosulfonic-Functionalzed Mesostructured Materials"—Chem. Rev., vol. 106, 2006, pp. 3790-3812.

Meng, Y. et al.—"Ordered Mesoporous Polymers and Homologous Carbon Frameworks: Amphiphilic Surfactant Templating and Direct Transformation"—Angew. Chem. Int. Ed., col. 44, 2005, pp. 7053-7059.

Meng. Y. et al.—"A Family of Highly Ordered Mesoporous Polymer Resin and Carbon Structures from Organic-Organic Self-Assembly"—Chem. Mater., vol. 18, 2006, 18 pages.

Mercier, L. et al.—"Heavy Metal Ion Adsorbents Formed by the Grafting of a Thiol Functionality to Mesoporous Silica Molecular Sieve: Factors Affecting Hg(11) Uptake"—Environ. Sci. Technol., vol. 32, 1998, pp. 2749-2754.

Molenkamp, W.C. et al.—"Highly Polarized Luminescence from Optical Quality Films of a Semiconducting Polymer aligned within Oriented Mesoporous Silica"—Journ. Am. Chem. Soc, vol. 126, 2004, pp. 4476-4477.

Moller, K. et al.—"Inclusion Chemistry in Periodic Mesoporous Hosts"—Chem. Mater., vol. 10, 1998, pp. 2950-2963.

Montanari, L. et al.—"Nuclear Magnetic Resonance Studies of Surface Interactions between Trifluoromethanesulfonic Acid and Silica"—Appl. Magn. Reson., vol. 12, 1997, pp. 329-339.

Muller, C.A. et al—"Amine-modified titania-silica hybrid gels as epoxidation catalysts"—Applied Catalysts A: General 201, 2000, pp. 253-261.

Pekala, R.W.—"Organic aerogels from the polycondensation of resorcinol with formaldehyde"—Journ. of Mater. Sci., vol. 24, 1989, pp. 3221-3227.

Petkov, N. et al.—"Functionalized cubic mesostructured silica films"—Materials Science and Engineering C, vol. 23, 2003, pp. 827-831.

Rodman, D.L. et al.—"Optical Metal Ion Sensor Based on Diffusion Followed by an Immobilizing Reaction. Quantitative Analysis by a Mesoporous Monolith Containing Functional Groups"—Anal. Chem., vol. 77, 2005, pp. 3231-3237.

(56) References Cited

OTHER PUBLICATIONS

Sayari, A. et la.—"Periodic Mesoporous Silica-Based Organic-Inorganic Nanocomposite Materials"—Chem. Mater., vol. 13, 2001, pp. 3151-3168.

Soler-Illia et al.—"Hybrid Mesoporous Films: An Organised Functional Nanofacility"—Journ. Chem. Eur, vol. 12, 2006, pp. 4478-4494.

Stein, A. et al.—"Hybrid Inorganic-Organic Mesoporous Silicates—Nanoscopic Reactors Coming of Age"—Adv. Mater., vol. 12, No. 19, Oct. 2000, pp. 1403-1419.

Tanaka, S. et al.—"Incorporation of Organic Groups within the Channel Wall of Spin-On Mesostructured Silica Films by a Vapor Infiltration Technique"—Langmuir, vol. 20, 2004, pp. 3780-3784.

Vega, A.J.—"Heteronuclear Chemical-Shift Correlations of Silanol Groups Studied by Two-Dimensional Cross-Polarization/Magic Angle Spinning NMR"—Jour. Am. Chem. Soc, vol. 110, 1988, pp. 1049-1054.

Wachs, I.E.—"Recent conceptual advances in the catalysis science of mixed metal oxide catalytic materials"—Catalysis Today 100, 2005, pp. 79-94.

Wasilike, J. et al.—"Concurrent Tandem Catalysis"—Chem. Rev., vol. 105, 2005, pp. 1001-1020.

* cited by examiner

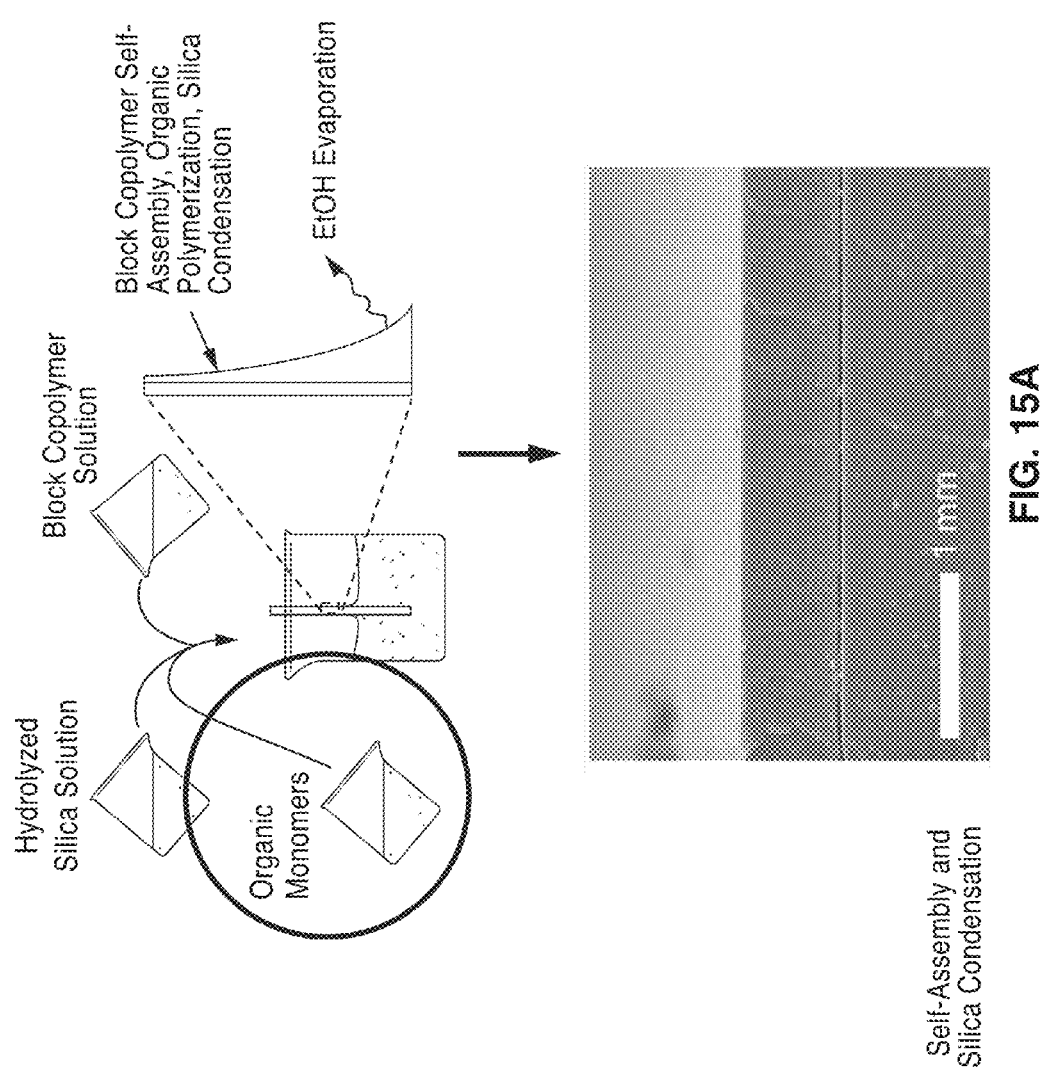

MOLECULAR OPTIMIZATION OF MULTIPLY-FUNCTIONALIZED MESOSTRUCTURED MATERIALS

CROSS-REFERENCE TO RELATED APPLICATIONS

This application claims priority to U.S. provisional patent application Ser. No. 61/183,485 filed on Jun. 2, 2009, incorporated herein by reference in its entirety.

STATEMENT REGARDING FEDERALLY SPONSORED RESEARCH OR DEVELOPMENT

This invention was made with Government support under Grant No. DAAD19-01-1-0121, awarded by the U.S. Army Research Office. The Government has certain rights in this invention.

INCORPORATION-BY-REFERENCE OF MATERIAL SUBMITTED ON A COMPACT DISC

Not Applicable

BACKGROUND OF THE INVENTION

1. Field of the Invention

The present disclosure relates generally to mesostructured materials and methods of preparing mesostructured materials. More specifically, the present disclosure relates to multiply-functionalized mesostructured films and methods of preparing multiply-functionalized mesostructured films.

2. Description of Related Art

Functionalization of porous inorganic solids can be used to produce materials with novel properties that derive from their heterogeneous structures and diverse compositions. Different functionalities can be combined to introduce properties that can be additive or have synergistic local effects. In heterogeneous catalysis, this has a long history, as exploited for example in metal/acid, bimetallic, and more recently tandem catalyst systems, which typically have been in the form of powders, e.g., zeolite molecular sieves, amorphous or crystalline metal oxides or mesoporous solids. Recently, processing opportunities presented by block-copolymer-directed mesostructured solids have led to materials in film, fiber, and monolith morphologies that have been functionalized with multiple species to obtain different property combinations. In many syntheses, emphases have been placed on so-called "one-pot" protocols in which multiple components, including functional species, are incorporated simultaneously during self-assembly and formation of the inorganic network. These, however, rely on the collective compatibilities of the various components under the synthesis conditions used, which often limits the extent and diversity of the functionalities that can be introduced.

Organic functionalization of mesoporous inorganic materials in particular has attracted considerable attention, due to the attractiveness of combining a wide range of organic compound properties with the robust thermal and mechanical stabilities of high surface area inorganic solids. The anchoring of organic moieties to mesoporous inorganic surfaces by covalent bonds has generally followed two protocols, either by co-condensation of the functional species as the inorganic framework cross-links or by post-synthetic grafting of the species to accessible pore surfaces after the framework has been formed. Siliceous frameworks have been frequently prepared, due to the versatility of silica sol-gel chemistry, compatibility of soluble precursors with block-copolymer self-assembly agents, and suitability of condensed networks for post-synthesis grafting or modification. In the case of silica, co-condensation involves the simultaneous cross-linking of hydrolyzed tetraalkoxysilanes $((RO)_4Si)$ with hydrolyzed trialkoxyorganosilanes $((RO)_3SiR')$, where $R'$ is an organic moiety), which in the presence of a structure-directing surfactant agent, yields mesostructured organically-modified silica. While co-condensation leads to the incorporation of the functional species in a single process step, removal of the surfactant species is usually required to produce the porosity needed to allow access to the functional sites in the mesopore channels. High concentrations of the precursor species tend to disrupt mesostructural ordering and make it difficult to control particle or other bulk (e.g., film, fiber, or monolith) morphologies. Additional challenges arise as the synthesis mixtures become more complicated, for example when additional co-solvent or functional species are present, due to the often competing or incompatible conditions required for their co-assembly.

In contrast, post-synthesis grafting methods are based primarily on the reactions of organosilanes $((R'O)_3SiR)$ or halosilanes (e.g., $Cl_3SiR$) with silanol groups on the interior mesopore channels of separately prepared (e.g., self-assembled and then calcined or solvent-extracted) mesoporous silica. This functionalization approach allows for a wide range of organic species to be anchored to silica surfaces without significantly affecting the mesostructural ordering of the silica support. Furthermore, the versatile processability of mesostructured block-copolymer-directed silica permits facile control over particle, film, fiber, or monolith morphologies and separate surface incorporation of multiple functional species, as will be shown below.

Accordingly, there is a need for a system and method for preparing mesostructured materials that have multiple functionalized locations within the structure that is easily constructed, inexpensive to produce, and has predictable functionality. The present constructs and methods satisfy these needs, as well as others, and are generally an improvement over the art.

BRIEF SUMMARY OF THE INVENTION

The present invention pertains to methods and systems that produce multiply functionalized materials that can be adapted for a variety of uses, such as electrodes, ultra-capacitors, fuel cell membranes, batteries, microelectronic or opto-electronic applications, ion-conduction applications and the like.

An example of multiply-functionalized inorganic materials is provided that uses cubic mesostructured aluminosilica with strong acid moieties that, as films, impart technologically attractive proton-conduction properties at elevated temperatures. Among the challenges to preparing such materials are the incompatibilities of the synthesis conditions required to incorporate the different individual functional components into the mesostructured films. Block-copolymer-directed silica mesophases can be formed from strongly acidic solutions, which allow highly ordered cubic mesostructured silica films to be synthesized. After calcination to remove the block-copolymer species, hydrophilic aluminosilica surface moieties can be introduced to the interior mesopore channels under highly alkaline solution conditions, followed by separate covalent grafting of perfluorinated-sulfonic-acid (PFSA) groups from non-aqueous solvents to introduce ion-conducting properties. This sequential synthesis protocol overcomes several previously severe materials limitations to yield complex materials with robust interconnected channels in films that can sustain high proton-conducting properties above 120° C. Under such conditions, these membranes maintain high proton conductivities that permit operation of hydrogen fuel cells at temperatures where CO poisoning of the anode catalyst and membrane dehydration are otherwise severely limiting.

Crucially, the properties of multiply-functionalized mesostructured silica films can be enhanced by consideration and optimization of important heterogeneities in local material compositions and structures. These include heterogeneities in the types, reactivities, and/or distributions of surface grafting sites, whose differences allow the introduction, coexistence, and optimization of complicated functionalities that are not generally achievable under a common set of synthesis conditions or in conventional membrane materials, such as those based on polymers.

Generally, sequenced-processing strategies can be combined with detailed characterization over multiple length scales, especially at a molecular level, to design and optimize complex new multifunctional solids with combinations of properties that have not been previously possible to obtain in a single ion-conducting material. A series of discrete synthesis steps under otherwise mutually incompatible conditions, e.g., from acidic, alkaline, and/or non-aqueous solutions, allows different functionalities to be introduced and optimized by using molecular-level understanding obtained from powerful two-dimensional (2D) solid-state correlation NMR techniques. Such methods are sensitive to local interactions among different surface moieties and thus yield detailed insights on the proximities and distributions of the different molecular components. Combined with complementary techniques, such as small-angle X-ray diffraction, electron microscopy, elemental analyses, and adsorption and conductivity measurements, new understandings of coupled and often competitive molecular interactions can be correlated and controlled to enhance macroscopic proton conductivities and thermal stabilities.

Sequential processing of multiply-functionalized mesoporous films is shown to yield materials that are compositionally and structurally heterogeneous on mesoscopic and molecular length scales, both of which must be controlled to maximize their macroscopic ion-conduction properties at elevated temperatures. To illustrate, cubic mesoporous silica films were prepared from strongly acidic solutions were separately functionalized under highly alkaline conditions to incorporate hydrophilic aluminosilica moieties and under non-aqueous conditions to introduce perfluorosulfonic-acid surface groups. Such sequential combination of individually incompatible steps yielded stable mesoporous films with high surface hydrophilicities and strong acid functionalities that exhibit high proton conductivities (ca. $2\times10^{-2}$ S/cm) at elevated temperatures (120° C.). Variable-temperature two-dimensional solid-state nuclear magnetic resonance (NMR) spectra reveal separate surface adsorption and grafting sites for the different functional surface species within the mesopore channels. $^{27}Al\{^{19}F\}$ and $^{29}Si\{^{19}F\}$ HETeronuclear chemical-shift CORrelation (HETCOR) NMR spectra establish that proton-conducting perfluorosulfonic-acid and pore-filling triflic acid ($F_3CSO^3H$) species are incorporated selectively onto different interior mesopore surface sites at $Q^3$ silica and six-coordinate $^{27}Al$ aluminosilica moieties, respectively. $^{27}Al\{^1H\}$ and $^{29}Si\{^1H\}$ HETCOR spectra show that adsorbed water molecules are associated with six-coordinate $^{27}Al$ aluminosilica and $Q^3$ silica sites, the former of which account for high water retention by the materials. The hydrophilic aluminosilica and acidic fluoro-group loadings and interaction sites are affected to different extents by the different synthesis and functionalization treatments, which were separately and collectively optimized to maximize the proton conductivities. Molecular, mesoscopic, and macroscopic properties of the multiply-functionalized films were monitored and correlated at each stage of the syntheses by NMR, small-angle X-ray scattering (SAXS), transmission electron microscopy (TEM), elemental analysis, adsorption, and conductivity measurements.

Accordingly, an aspect of the invention is a sequential method of forming a multiply functionalized mesostructured material, the method comprising: providing a mesostructured material; performing a first processing step to introduce a first functional property into a mesostructured material under a first set of process conditions; and performing a second processing step to introduce a second functional property into the mesostructured material under a second set of process conditions, the second set of process conditions being different from the first set of process conditions. Optionally, one or more additional processing steps can be performed to introduce one or more additional functional properties into the mesostructured material under one or more additional sets of process conditions, the additional set(s) of process conditions being different from the first set of process conditions.

In one embodiment, the first processing step may involve self-assembly of a silica (or organosilica) framework that is mesostructured (the periodic ordering of which can be modified), yields (modifiable) porosity, has certain (modifiable) mechanical properties, and has certain (modifiable) surface reaction properties that allow subsequent additional functional agents (e.g., aluminosilica or perfluoro-sulfonic acid moieties) to be incorporated. In one embodiment, the modifiability of the silica (or organosilica or other) framework enables additional functional agents to be incorporated (and optimized). In one embodiment, the framework itself is considered to be "functional" in the above ways with respect to its modifiability or functionalizability.

Another aspect of the invention is a method of forming mesostructured materials with multiple functionalities that are independently adjustable and collectively optimizable, comprised of sequential processing steps that include a process selected from the group consisting of casting, spin- or dip-coating, self-assembly, polymerization, solvent extraction, calcination, or adsorption of functional agents as is, or in the presence of organic and/or inorganic species, wherein one or more of the processes are converted into an organic and/or inorganic network.

Another aspect of the invention is to provide a method that collectively optimizes the first, second, and any subsequent sets of process conditions to obtain an optimized combination of first, second, and subsequent functionalities. Likewise, the first, second, and subsequent sets of process conditions can be independently adjusted to control the first, second, and subsequent functional properties.

A further aspect of the invention is a multiply functionalized mesostructured material comprising a first functional agent that provides a first functional property and a second functional agent that provides a second functional property. Optionally, the invention can include additional functional agents that provide optional additional functional properties.

A still further aspect of the invention is a multiply functionalized mesostructured material comprising a first functional agent that provides a first functional property and a second functional agent that provides a second functional property, wherein the multiply functionalized mesostructured material is prepared by a process comprising: performing a first processing step to introduce a first functional property into a mesostructured material under a first set of process conditions; and performing a second processing step to introduce a second functional property into the mesostructured material under a second set of process conditions, the second set of process conditions being different from the first set of process conditions. Optionally additional functional agents provide additional functional properties. Optionally additional processing steps may be performed to introduce additional functional properties into the mesostructured material under additional sets of process conditions, the additional sets of process conditions being different from the first or immediately preceding sets of process conditions.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 4A:
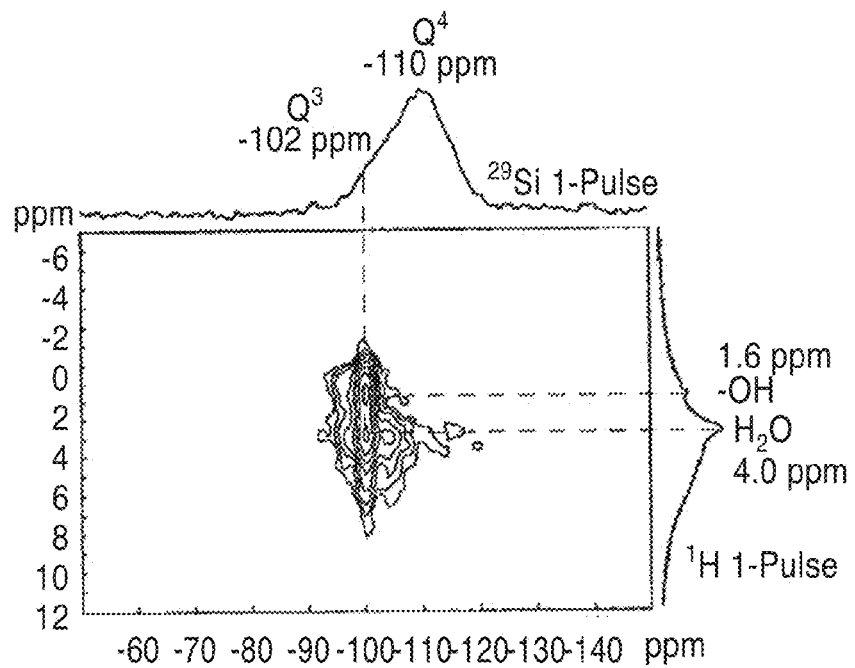
FIG. 4A is a solid-state 2D $^{29}$Si{$^1$H} HETCOR NMR spectrum acquired at −30° C. (6 kHz MAS) of a powder sample prepared from the same cubic mesoporous PFSA-grafted (5 wt % PFSA) aluminosilica (3.5 wt % Al) film containing 8 wt % F$_3$CSO$_3$H acid backfilling the mesopores, as shown in FIG. 3C and Table 1.
Figure 4B:
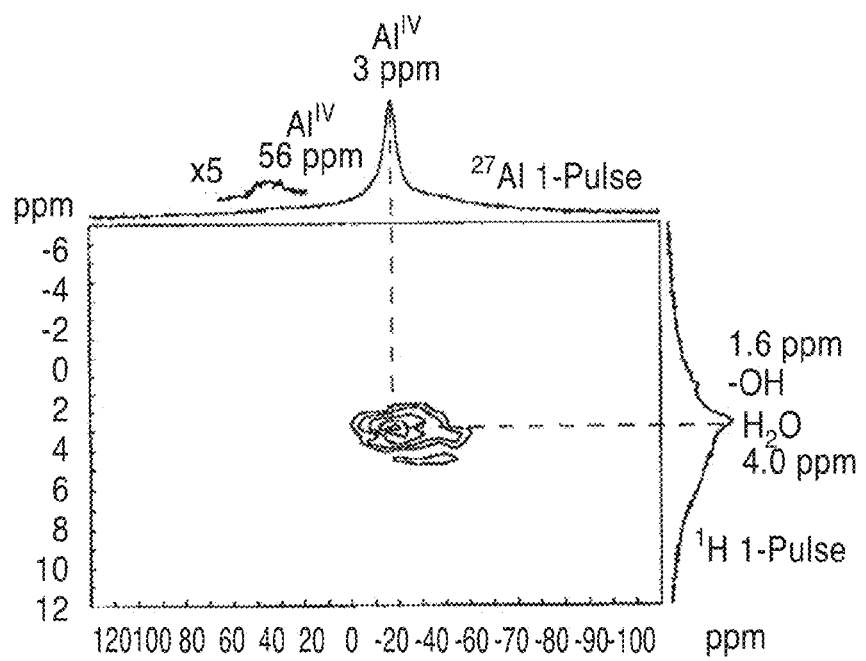
FIG. 4B is a solid-state 2D $^{27}$Al{$^1$H} HETCOR NMR spectrum acquired at −30° C. (6 kHz MAS) of a powder sample prepared from the same cubic mesoporous PFSA-grafted (5 wt % PFSA) aluminosilica (3.5 wt % Al) film containing 8 wt % F$_3$CSO$_3$H acid backfilling the mesopores, as shown in FIG. 3C and Table 1.
Figure 5A:
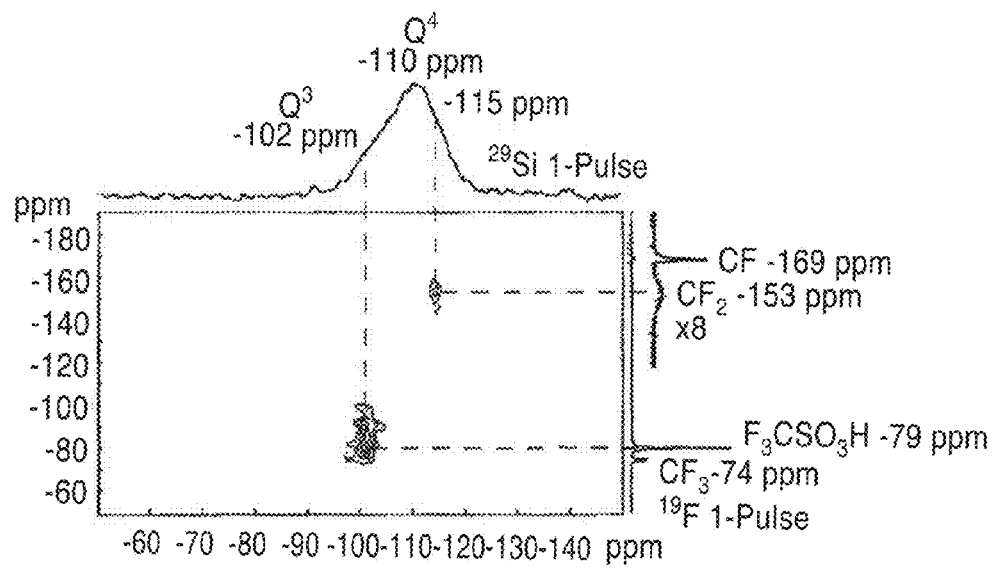
FIG. 5A is a solid-state 2D $^{29}$Si{$^{19}$F} HETCOR NMR spectrum acquired at −30° C. (6 kHz MAS) for the same PFSA-grafted (5 wt % PFSA) cubic mesoporous aluminosilica (3.5 wt % Al) films containing 8 wt % F$_3$CSO$_3$H acid, that were examined in FIG. 3 and FIG. 4 and Table 1.
Figure 5B:
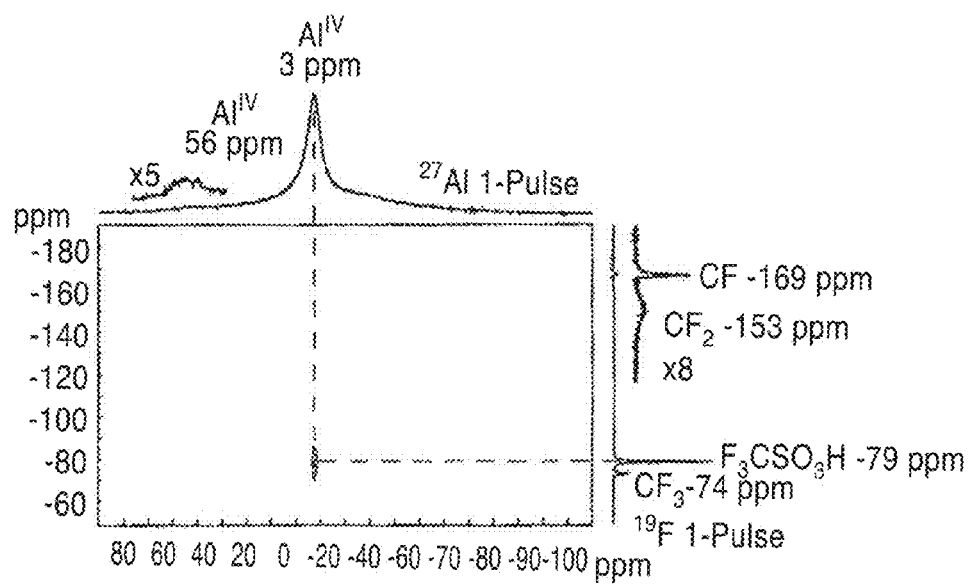

FIG. 5B is a solid-state 2D $^{27}$Al{$^{19}$F} HETCOR NMR spectrum acquired at −30° C. (6 kHz MAS) for the same PFSA-grafted (5 wt % PFSA) cubic mesoporous aluminosilica (3.5 wt % Al) films containing 8 wt % F$_3$CSO$_3$H acid, as examined in FIG. 2, FIG. 3 and Table 1. Separate single-pulse $^{29}$Si, $^{27}$Al, and $^{19}$F MAS NMR spectra are plotted along their corresponding axes in FIG. 4A and FIG. 4B. The $^{29}$Si{$^{19}$F} HETCOR spectrum shows strongly correlated signal intensities between surface framework $^{29}$Si sites and $^{19}$F nuclei of adsorbed triflic acid (F$_3$CSO$_3$H) and grafted perfluorosulfonic acid species, respectively. The $^{27}$Al{$^{19}$F} HETCOR spectrum shows correlated signal intensities between six-coordinate framework $^{27}$Al nuclei and $^{19}$F nuclei of the adsorbed triflic acid species.

Figure 6A:
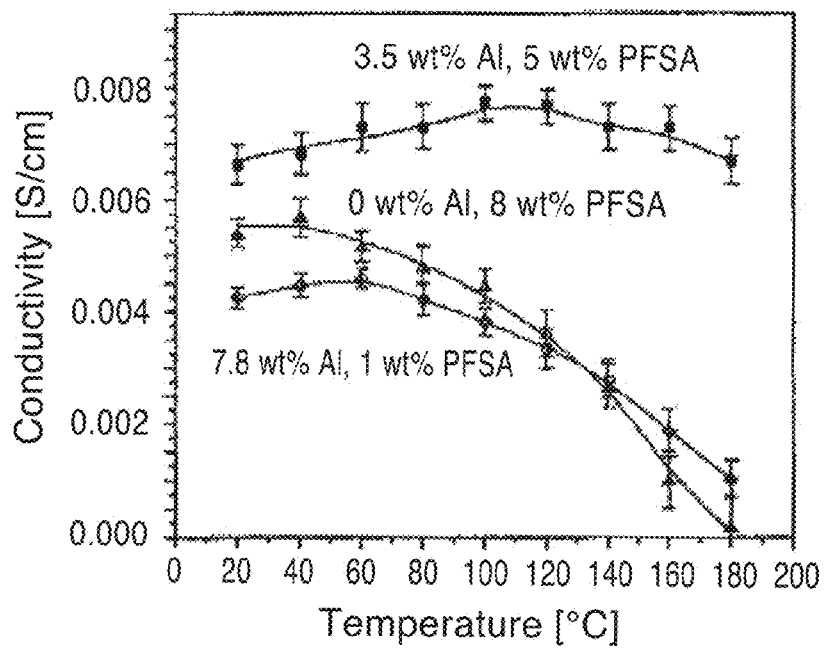

FIG. 6A is a graph of proton conductivities as a function of temperature at 50% relative humidity (RH) for identical 65-μm-thick cubic mesoporous silica films containing different concentrations of surface-grafted aluminosilica (Al) and perfluorosulfonic-acid (PFSA) moieties containing [♦] 7.8 wt % Al, 1 wt % PFSA; [■] 3.5 wt % Al, 5 wt % PFSA; or [▲] 0 wt % Al, 8 wt % PFSA used for optimization of aluminosilica- and PFSA-grafting concentrations and triflic-acid mesopore-filling concentrations in cubic mesoporous silica films.

Figure 6B:
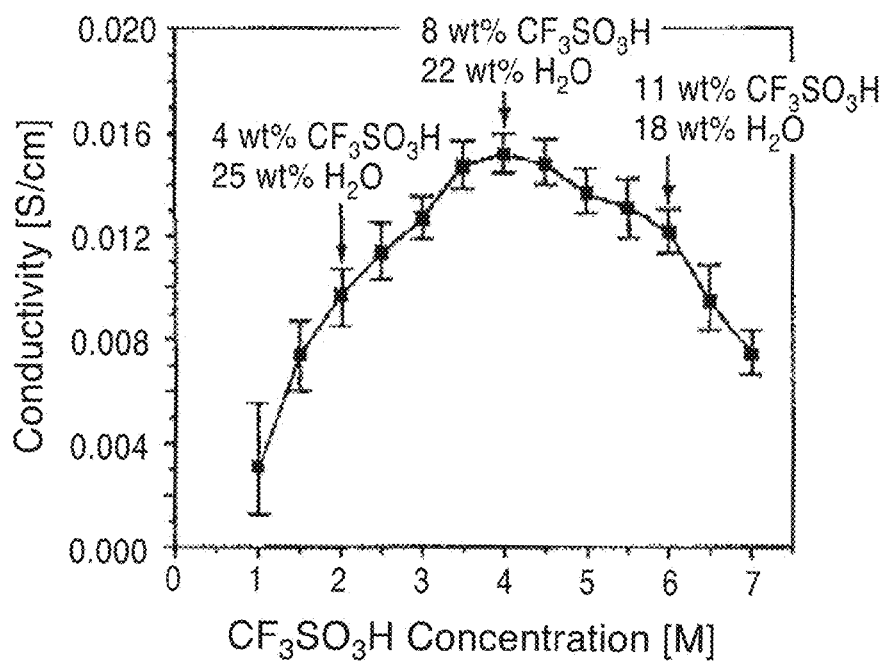

FIG. 6B is a graph of proton conductivity as a function of triflic acid mesopore-filling concentrations in free-standing 105-μm-thick 5 wt % PFSA- and 3.5 wt % Al aluminosilica-grafted cubic mesoporous silica films at ambient conditions (20° C. and ~40% RH).

Figure 6C:
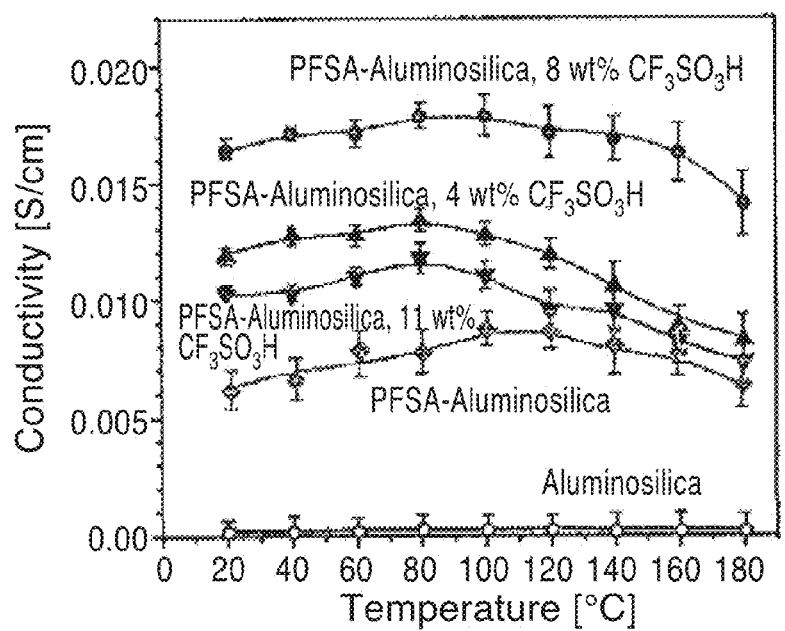

FIG. 6C is a graph of proton conductivity as a function of temperature at 50% RH for otherwise identical 65-μm-thick 5 wt % PFSA- and 3.5 wt % Al aluminosilica-grafted cubic mesoporous silica films containing different amounts of triflic acid back-filling the mesopores: [♦] 0 wt % F$_3$CSO$_3$H acid, [▲] 4 wt % F$_3$CSO$_3$H acid, [●] 8 wt % F$_3$CSO$_3$H acid, and [▼] 11 wt % F$_3$CSO$_3$H acid. The conductivity of [○] cubic mesoporous aluminosilica (3.7 wt % Al) without co-grafted-PFSA or triflic acid species is shown for comparison.

Figure 7A:
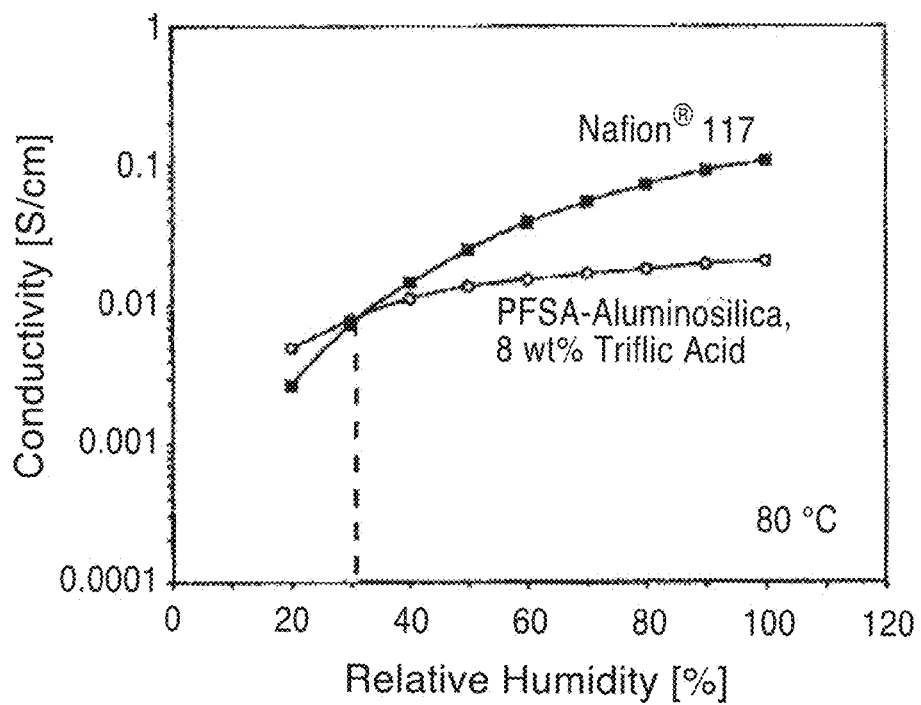
Figure 7B:
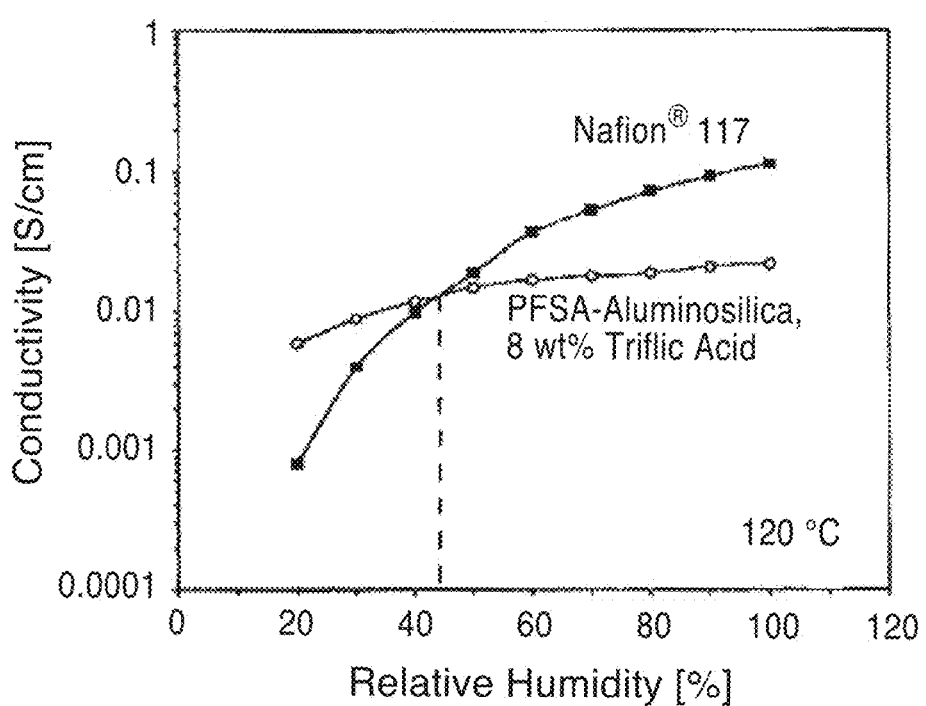
Figure 7C:
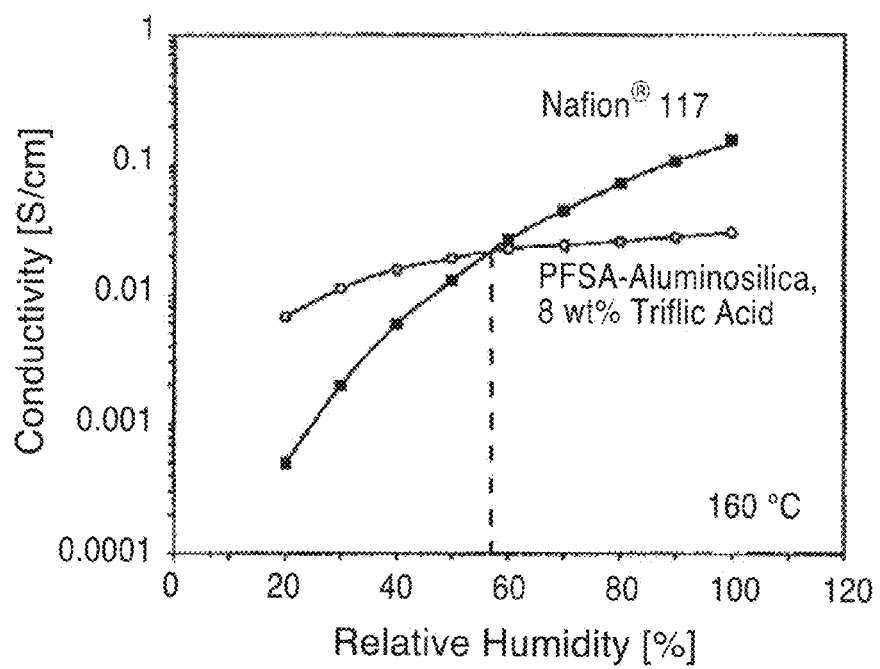

FIG. 7A through FIG. 7C are graphs of proton conductivity measured by AC impedance spectroscopy for an optimized perfluorosulfonic-acid-functionalized (5 wt % PFSA) cubic mesoporous aluminosilica (3.5 wt % Al) film containing 8 wt % triflic acid mesopore backfilling [○] and a Nafion® 117 membrane [■] as functions of relative humidity at (A) 80° C., (B) 120° C., and (C) 160° C. respectively.

Figure 8:
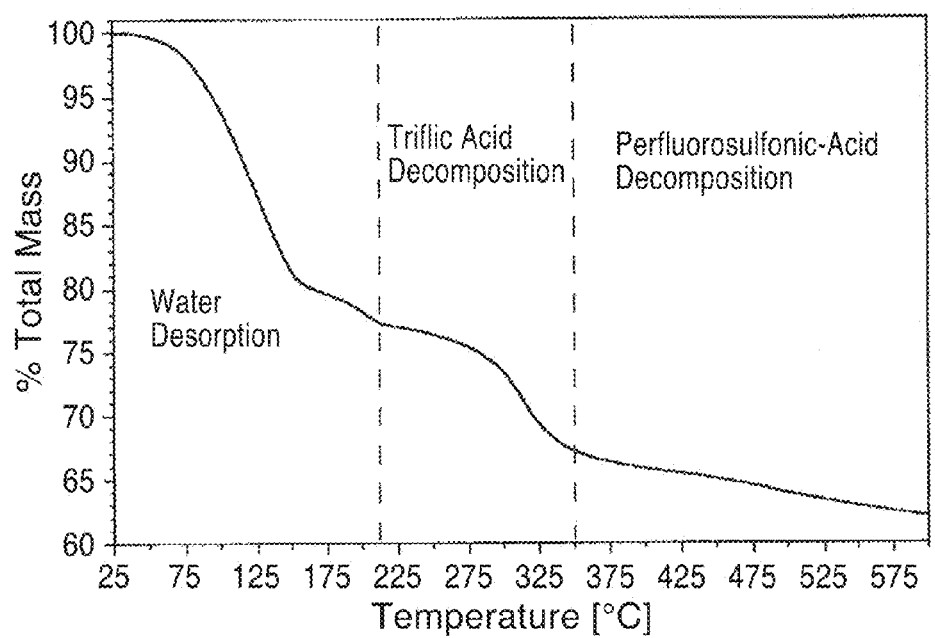

FIG. 8 is a graph of thermogravimetric analysis (TGA) of the perfluorosulfonic-acid-grafted (5 wt % PFSA) cubic mesoporous aluminosilica (3.5 wt % Al) film containing ~8 wt % triflic acid (F$_3$CSO$_3$H) backfilling the mesopores. Mass spectrometry analyses of the effluent gases shown in FIG. 14 allow for species identification and correlation to the various mass loss regions.

Figure 9:
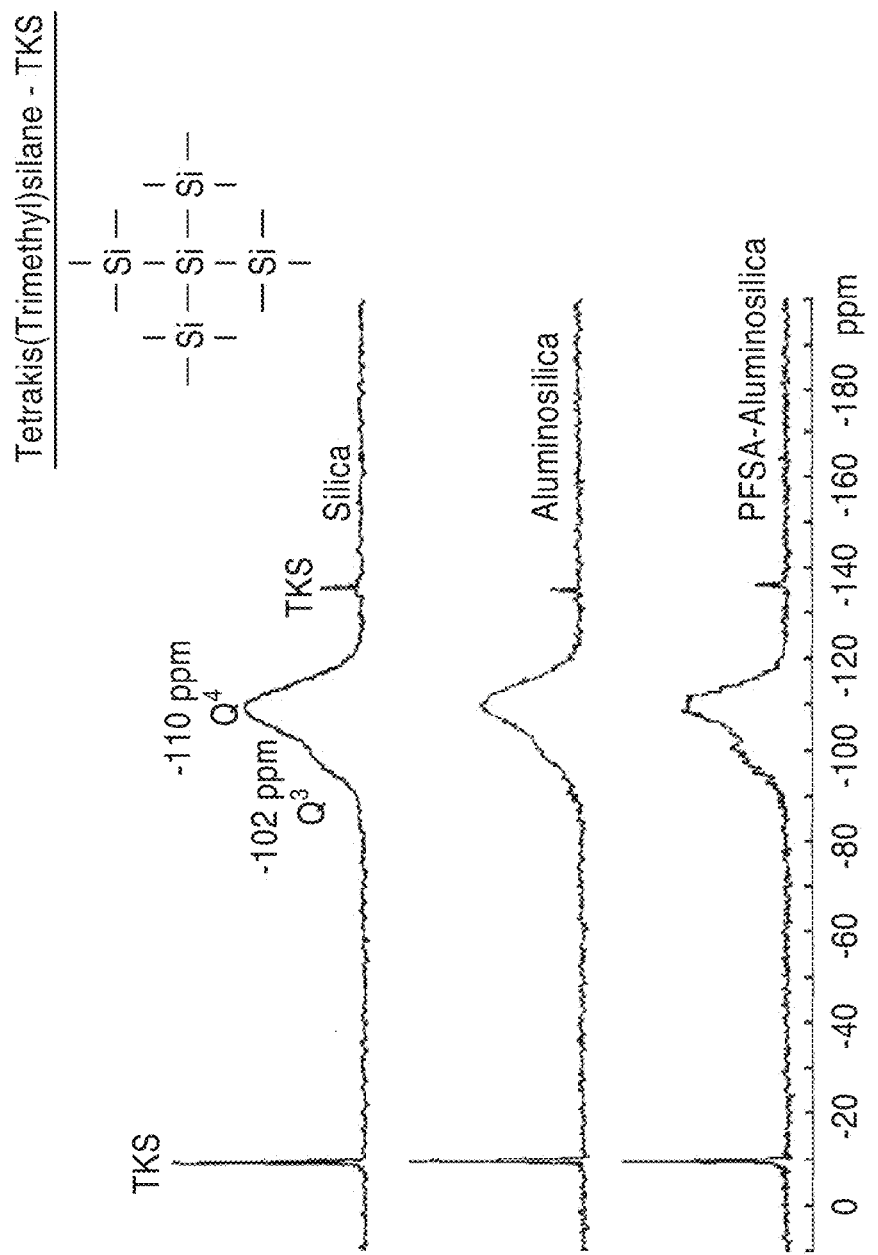

FIG. 9 is quantitative single-pulse $^{29}$Si MAS NMR spectra acquired for cubic mesoporous silica, aluminosilica (3.5 wt % Al), and PFSA-grafted (5 wt % PFSA) aluminosilica (3.5 wt % Al) film materials. All spectra were quantified using 2 mg tetrakis(trimethyl)silane (TKS) as an internal standard.

Figure 10A:
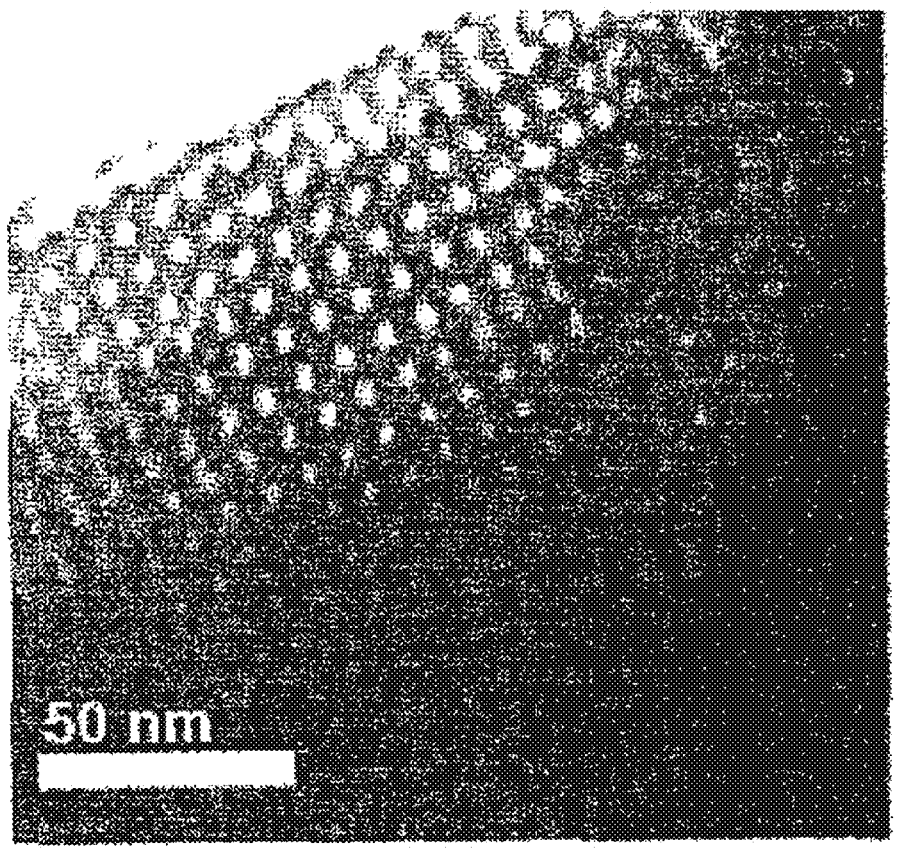
Figure 10B:
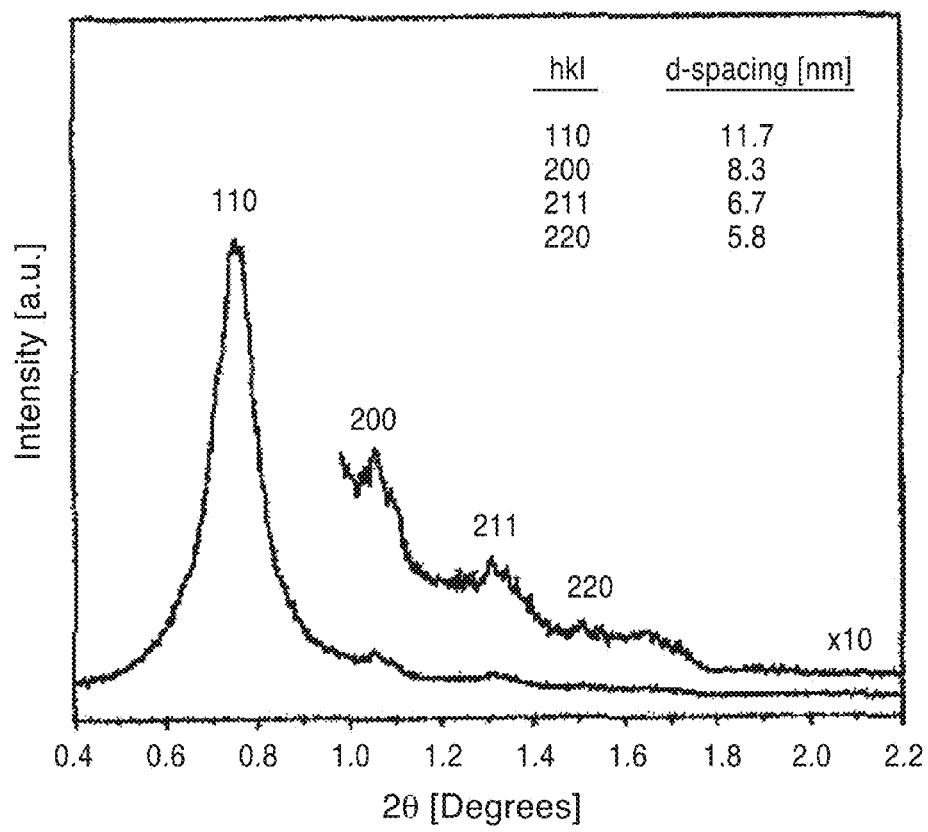

FIG. 10A is a transmission electron microscopy image and FIG. 10B is a small-angle X-ray scattering pattern for the perfluorosulfonic-acid-grafted cubic (5 wt % PFSA) mesoporous aluminosilica (3.5 wt % Al) film. The diffraction pattern is indexed to the body-centered-cubic (Im $\overline{3}$ m) structure. The 1D plot is the azimuthal integral of a 2D scattering pattern obtained by transmission mode XRD with the beam oriented perpendicular to the plane of the films.

Figure 11A:
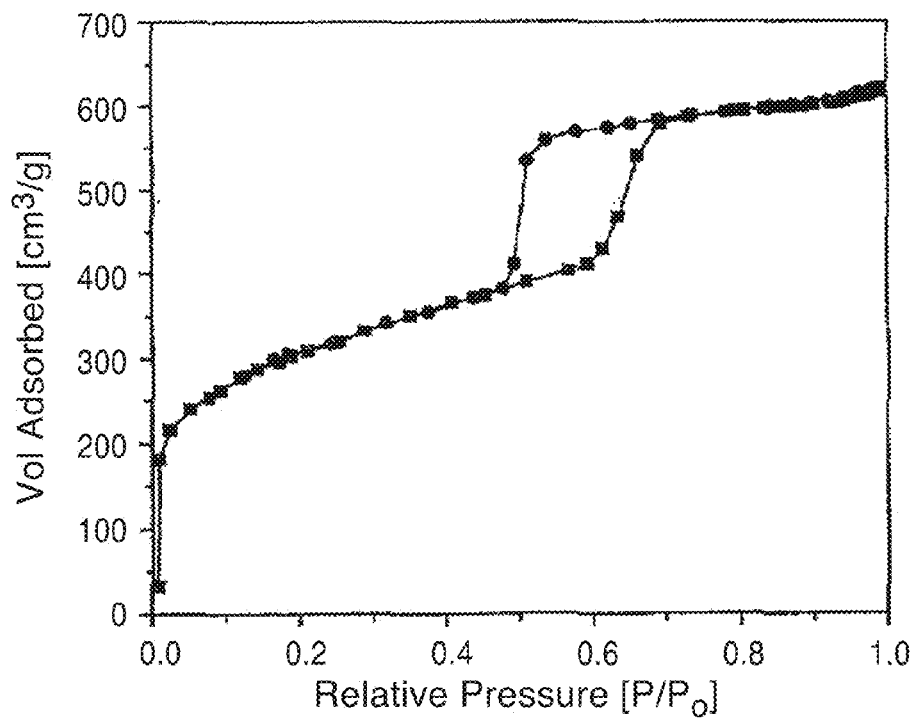
Figure 11B:
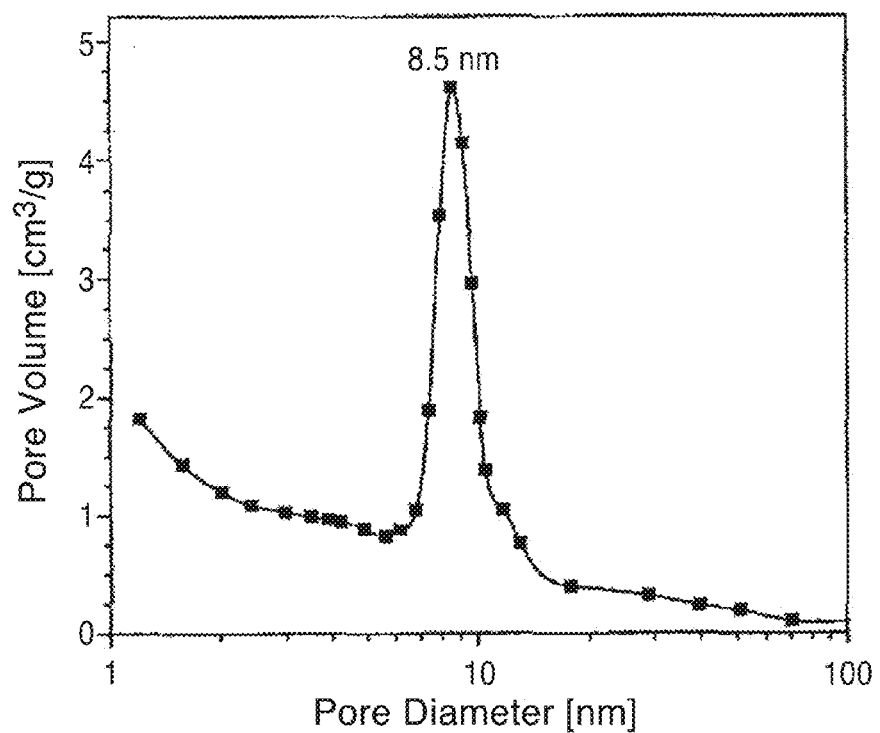

FIG. 11A is a graph of nitrogen adsorption [■]-desorption [●] isotherms acquired at 77 K and FIG. 11B is a mesopore-size-distribution plot obtained from a Barrett-Joyner-Halenda (BJH) analysis of the adsorption isotherm branch for the perfluorosulfonic-acid-grafted (5 wt % PFSA) cubic mesoporous aluminosilica (3.5 wt % Al) film material with body-centered-cubic (Im $\bar{3}$ m) ordering (no triflic acid).

Figure 12:
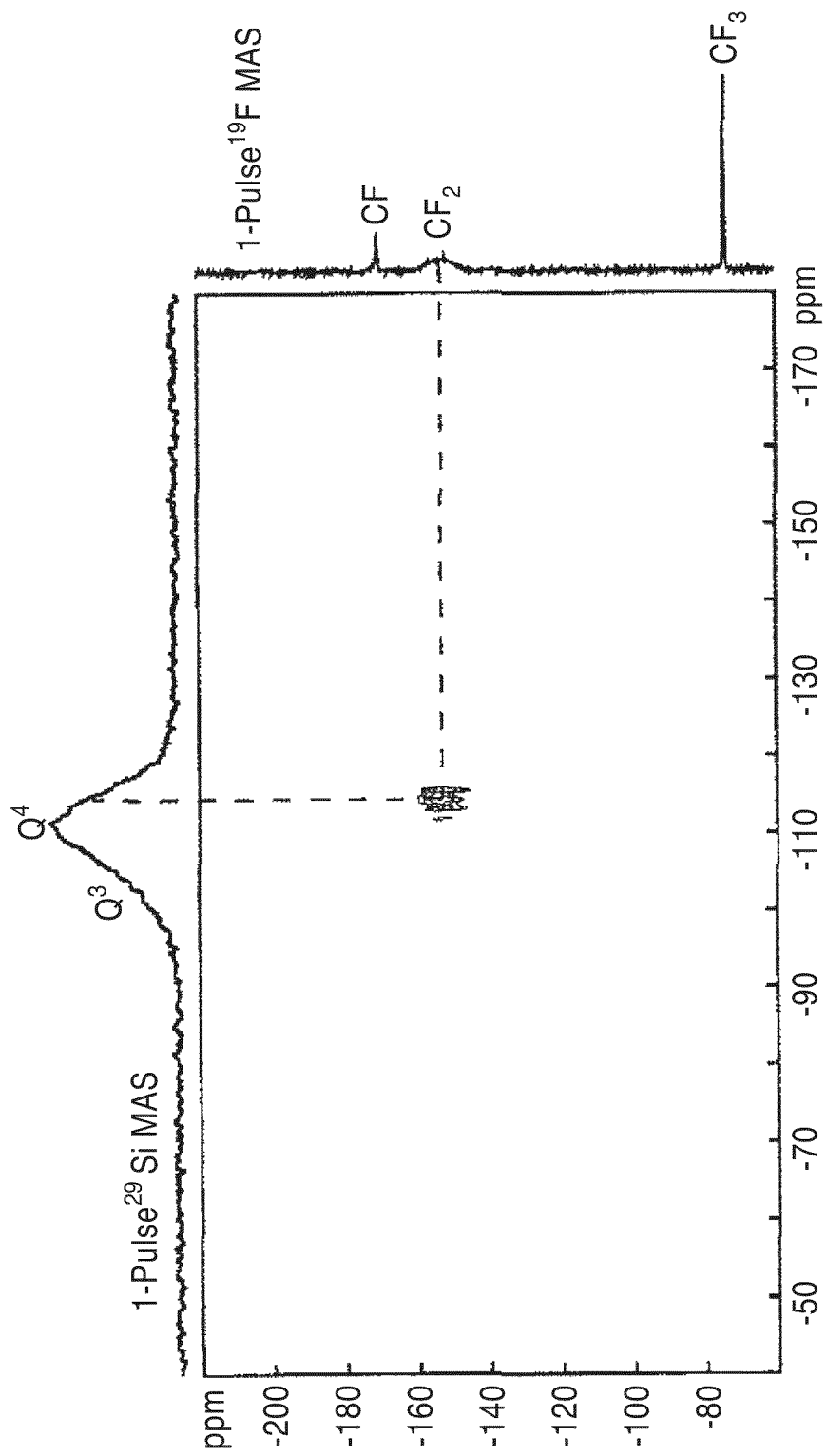

FIG. 12 is a solid-state 2D $^{29}$Si{$^{19}$F} HETCOR spectrum acquired at room temperature for the perfluorosulfonic-acid-grafted (5 wt % PFSA) cubic mesoporous aluminosilica (3.5 wt % Al) prior to backfilling of the mesopores with triflic acid. Separate single-pulse $^{29}$Si and $^{19}$F MAS spectra are plotted along their corresponding axes. The 2D HETCOR contour plot shows correlated signal intensity between the —$CF_2$— fluorine atoms of the grafted PFSA and surface $^{29}$Si moieties near the silica grafting site.

Figure 13:
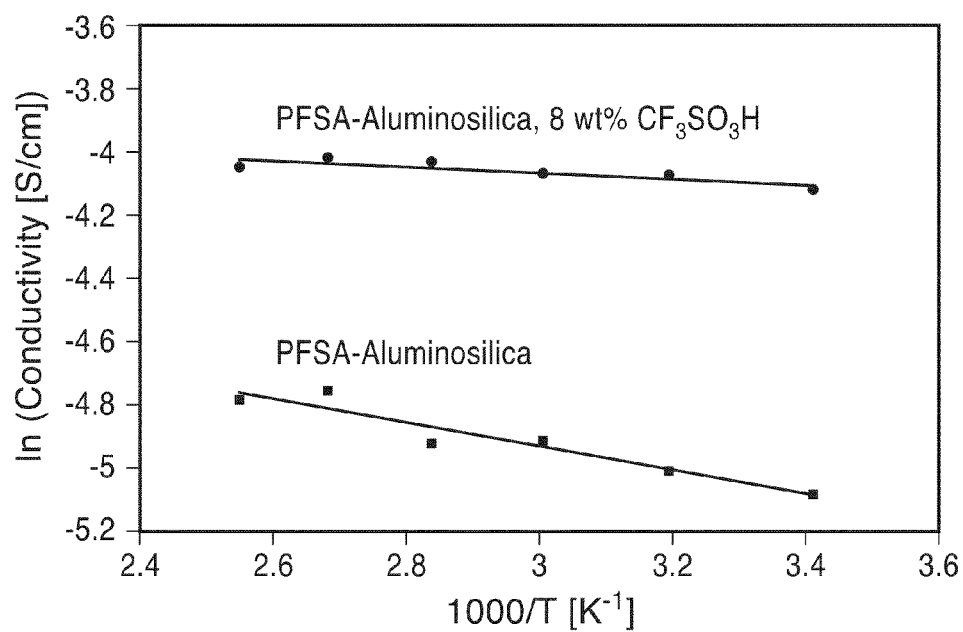
Figure 14A:
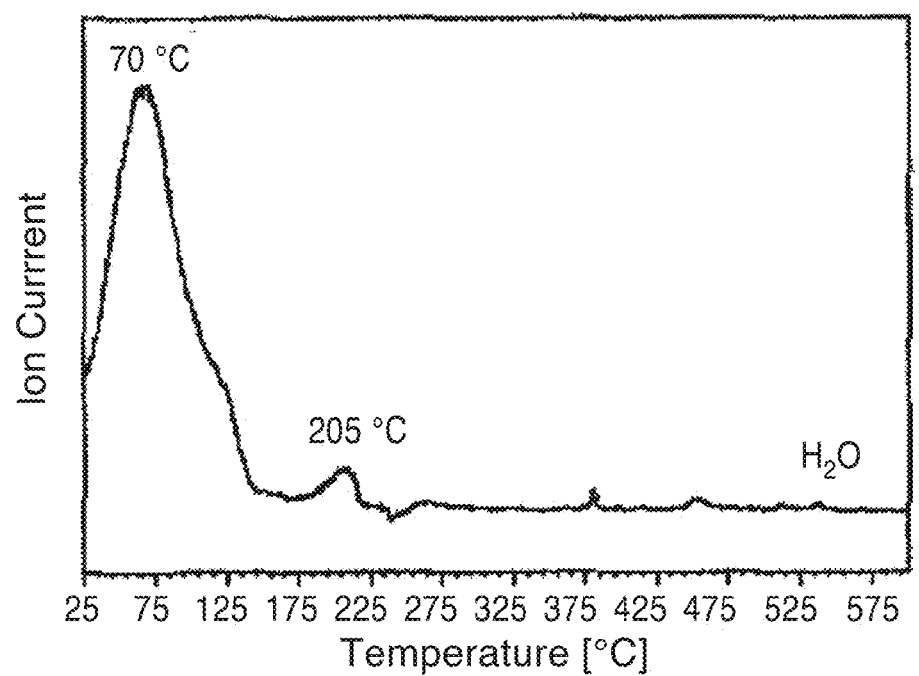
Figure 14B:
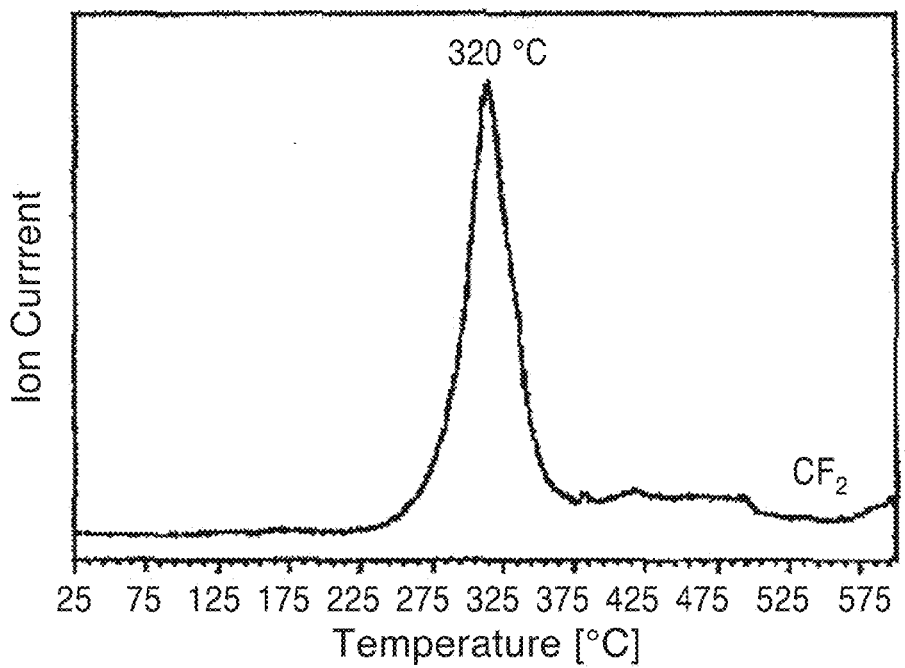
Figure 14C:
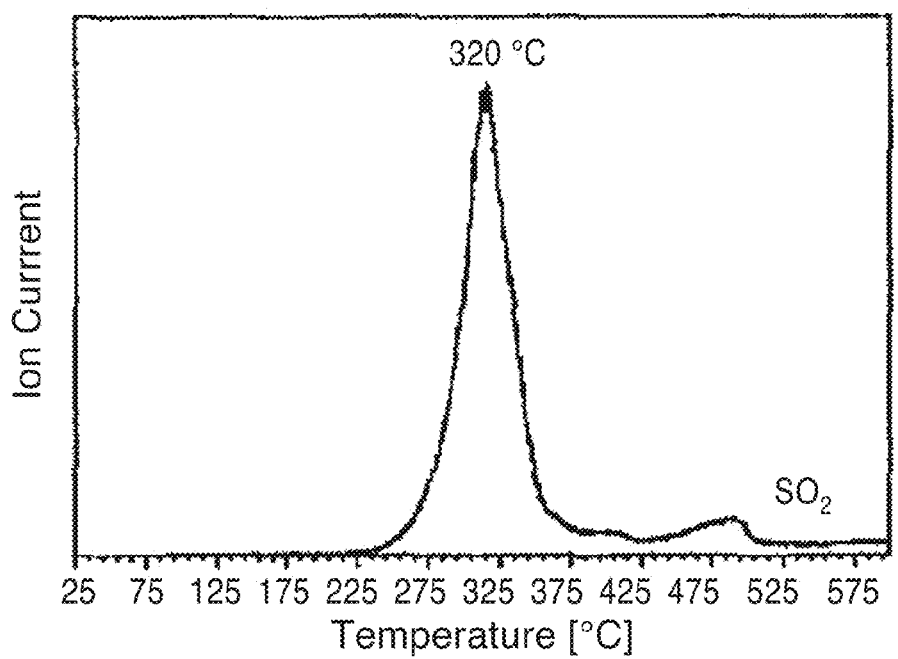
Figure 14D:
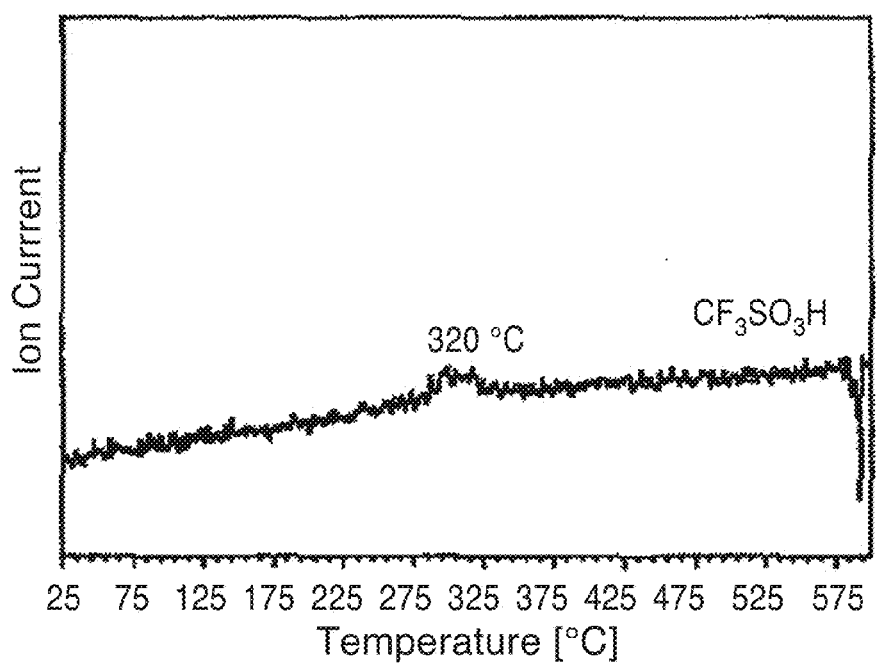

FIG. 13 are Arrhenius-type plots of proton conductivities measured as functions of temperature for the optimally functionalized PFSA-aluminosilica membranes without and with 8 wt % triflic acid corresponding to the data shown in FIG. 6C.

FIG. 14A through FIG. 14D show mass spectrometry measurements conducted simultaneously on the effluent gases from PFSA-grafted (5 wt % PFSA) aluminosilica (3.5 wt % Al) film containing 8 wt % triflic acid in the mesopores, as it was heated during thermogravimetric analysis to identify the temperature ranges over which (13A) $H_2O$, (13B) $CF_2$, (13C) $SO_2$, and (13D) $F_3CSO_3H$ species were responsible for specific mass losses in the material.

FIG. 15A is a schematic diagram illustrating the synthesis of mesostructured organosilica films.

Figure 15B:
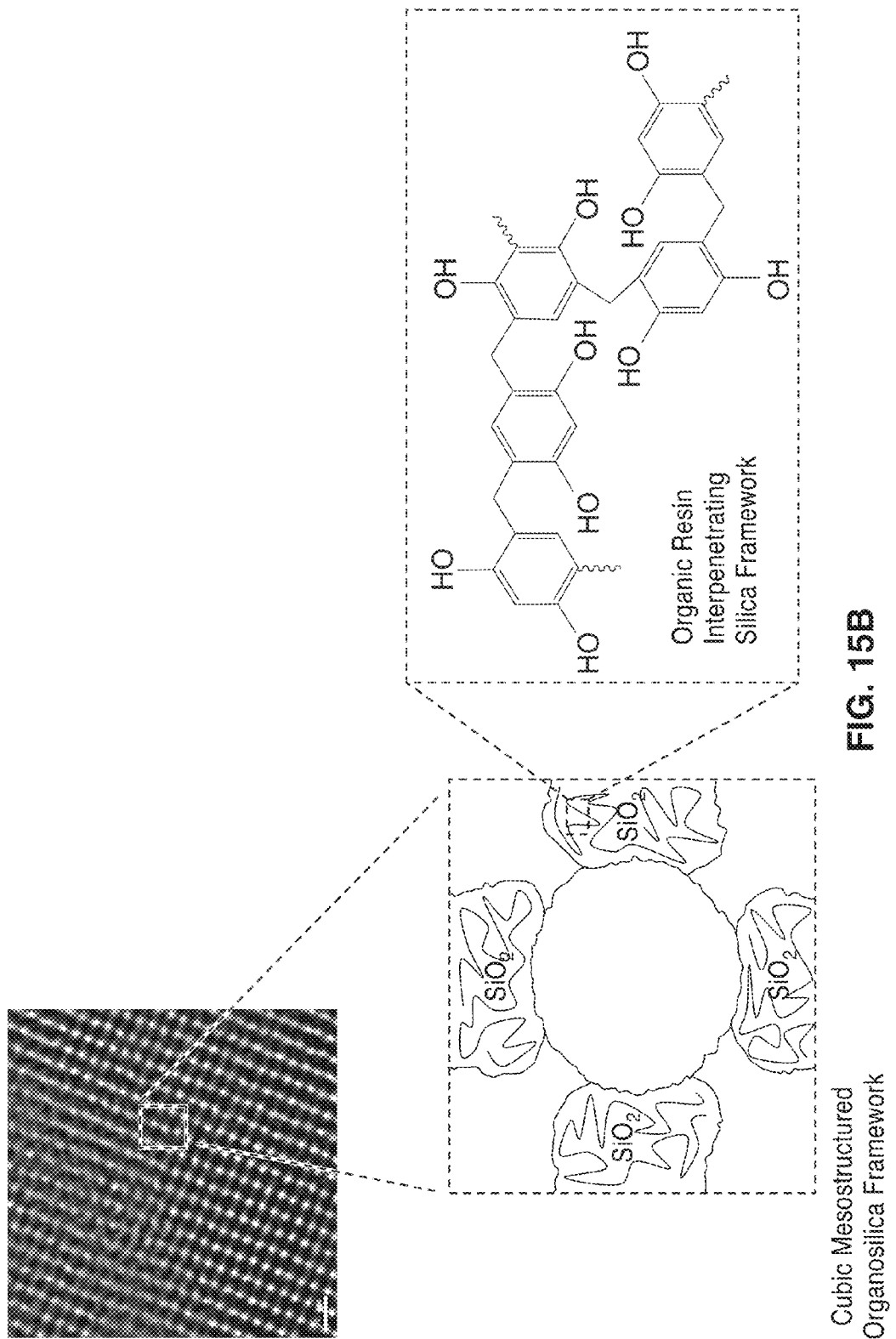

FIG. 15B is a transmission electron micrograph showing the high degree of cubic mesostructural ordering, accompanied by schematic diagrams of the mixed silica-resin framework and resin structure.

Figure 16:
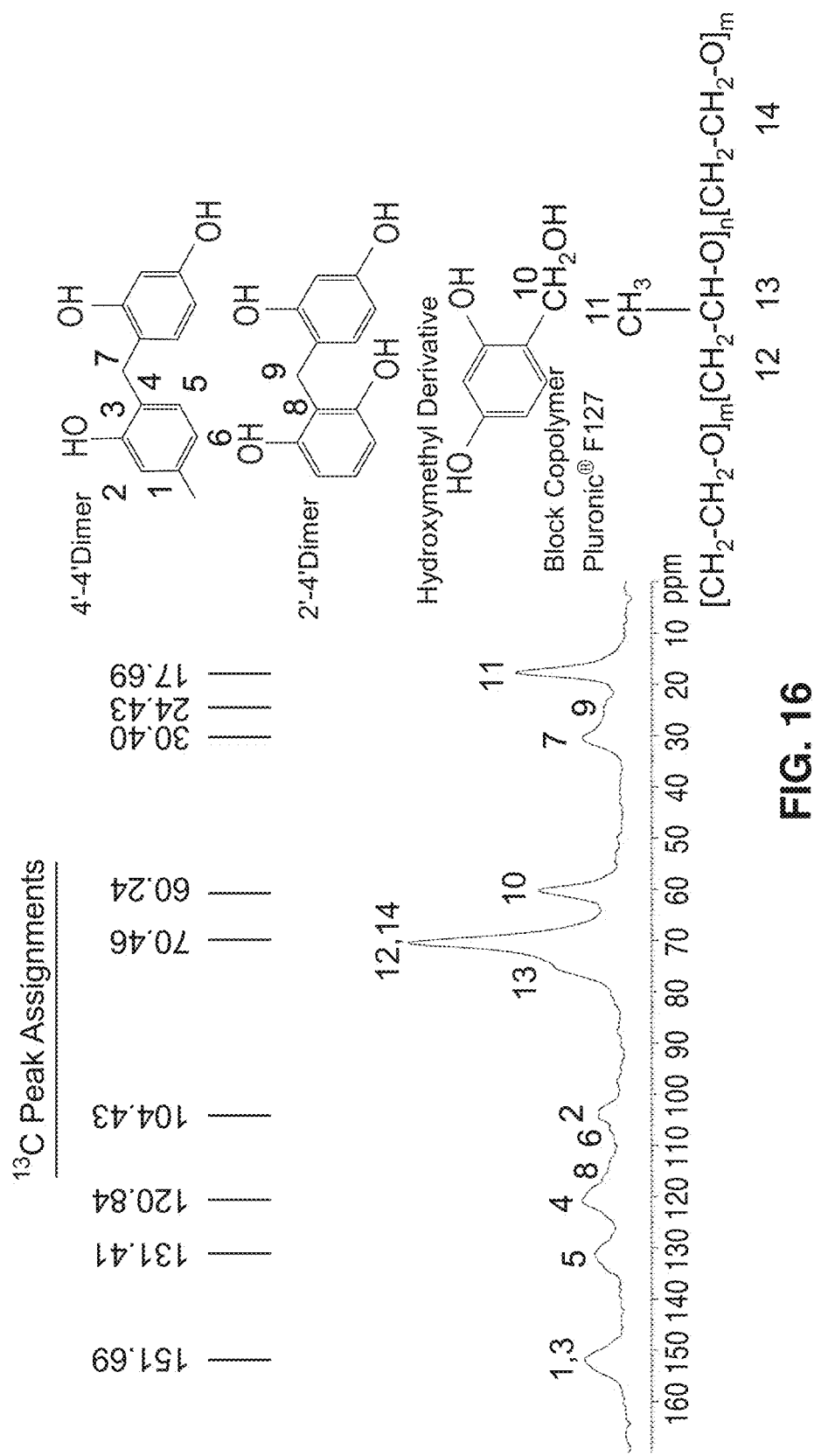

FIG. 16 is a $^{13}$C CP-MAS NMR spectrum of a mesoporous silica-resin film containing an initial mass ratio of organic precursor/TEOS mass ratio of 0.20 and thermally polymerized at 100° C. for 12 hours. The corresponding peak assignments and moieties associated with the F127 triblock copolymer species, organic resin, and oligomeric cross-linking products.

DETAILED DESCRIPTION OF THE INVENTION

Referring more specifically to the drawings, for illustrative purposes the present invention is embodied in the methods generally shown in FIG. 1 through FIG. 16 and the associated devices used to perform the methods. It will be appreciated that the devices and systems may vary as to configuration and as to the details of the parts, and that the method may vary as to the specific steps and sequence, without departing from the basic concepts as disclosed herein.

The present invention relates to methods for the production of multiply functionalized mesostructured materials for use in a variety of applications such as ultra-capacitors, electrodes, membranes, optoelectronic devices, electrocatalysts, or sensors.

The methods use sequential processing to yield novel multiply-functionalized mesostructured materials with macroscopic properties that can be optimized. Sequential processing allows individually incompatible synthesis or processing conditions to be used to introduce material functionalities that are impossible in a single-step synthesis procedure. The invention provides a method is a method of forming mesostructured materials with multiple functionalities that are independently adjustable and collectively optimizable.

For example, cubic mesostructured silica films prepared from strongly acidic solutions were subsequently and separately functionalized under highly alkaline conditions to incorporate hydrophilic aluminosilica moieties and then under non-aqueous conditions to introduce perfluorosulfonic-acid surface groups. Such sequential combination of these otherwise incompatible individual steps yielded stable mesoporous films with high surface hydrophilicities and strong acid functionalities that exhibited high proton conductivities at elevated temperatures. As another example, organosilica materials were synthesized with compositions and structures that can be optimized to obtain films, monoliths, fibers, or powder materials with novel combinations of mechanical, adsorption, transport, and/or other properties.

Figure 1:
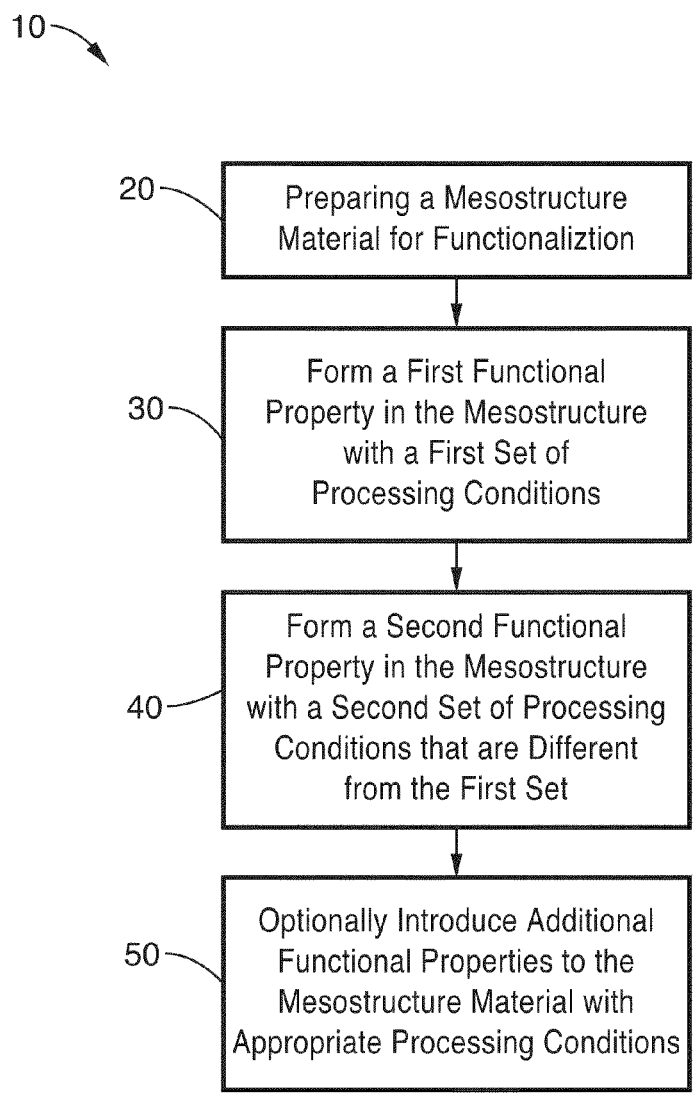
FIG. 1 is a schematic flow diagram of a method for producing a multiply functionalized mesostructured material according to one embodiment of the invention.

Turning now to the flow diagram show in FIG. 1, one embodiment 10 of the invention is schematically shown. At block 20, a mesostructured material is prepared for functionalization. The preferred mesostructured material is in the form of a film, but may also monoliths, fibers, or powder materials as well. Mesostructured materials typically have surface areas greater than 10 $m^2$/g.

Mesoporosity of the material can be produced through self-assembly of components or formed on a mesostructured framework of a network of organic species or inorganic species that is subsequently removed to yield a porous material. In one embodiment, organic and/or inorganic species are processed in the presence of one or more solvents. The organic species can be a surfactant or polymer species, including block-copolymers. For example, addition of an organic species may be incorporated over a range of approximately 0-50 wt % to adjust the mechanical, optical, optoelectronic, adsorption, transport, or reaction properties of the mesostructured material. Examples of suitable organic species include epoxy, resorcinol, phenol, organometallic, dye, or network-forming organic species known in the art. The organic species may be incorporated as monomers, oligomers, or form polymeric networks.

In one embodiment, the first processing step at block 20 preferably involves self-assembly of a silica or organosilica framework, where the periodic ordering of the mesostructure can be modified to yield a characteristic porosity. Silica is preferred because of its mechanical properties and surface reaction properties that can be modified to allow subsequent additional functional agents (e.g., aluminosilica or perfluorosulfonic acid moieties) to be incorporated. In one embodiment, the modifiability of the silica or organosilica or other framework enables additional functional agents to be incorporated and optimized. In another embodiment, the framework itself is considered to be "functional" in the above ways with respect to its modifiability or functionalizability.

In another embodiment, the inorganic species forming the mesoporous framework include mesostructured titania, alumina, and other oxides, nitrides, phosphides, carbides, chalcogenides, organometallic compounds, metalloxanes, or other soluble or colloidal species. In one embodiment, the mesostructured materials are in the form of patterned films on a substrate.

The initial step at block 20 may also have processing steps that include casting, spin- or dip-coating, self-assembly, polymerization, solvent extraction, calcination, or adsorption of functional agents as is, or in the presence of an organic and/or inorganic species, wherein one or more of the processes are converted into an organic and/or inorganic network.

The first functional property is introduced to the mesostructured material with a first set of process conditions at block 30 of FIG. 1. Illustrative functionalization at block 30 properties include hydrophilicity, hydrophobicity, ion-conduction, adsorption selectivity, chemical reactivity, transport, electrical conduction, mechanical, optical, or opto-electronic properties. Other functional properties can be used to provide certain functionalities according to the invention. Process conditions may include acidic, alkaline, or neutral aqueous conditions, non-aqueous solvents or gas-phase conditions.

A second processing step is applied at block 40 to introduce a second functional property to the mesostructure. Illustrative functionalization introduced at block 40 include: hydrophilicity, hydrophobicity, ion-conduction, adsorption selectivity, chemical reactivity, transport, electrical conduction, mechanical, optical, or opto-electronic properties. For example the first functional property could be a mechanical property and the second functional property could be an adsorption property.

It is preferred that the first processing step and the second processing step are different; and that the functional property introduced by the first processing step be different from the functional property introduced by the second processing step. However, this is not mandatory.

A variety of alternatives are available for functionalization of the mesostructure. For example, the first processing step may include acidic conditions and the second processing step may include alkaline conditions. Alternatively, the first processing step may include acidic conditions and the second processing step includes predominantly non-aqueous conditions. In another embodiment, the first processing step includes alkaline conditions and the second processing step includes predominantly non-aqueous conditions. In a further embodiment, the first processing step includes predominantly non-aqueous conditions and the second processing step includes predominantly non-aqueous conditions. In another embodiment, the first processing step is incompatible with the second processing step.

At block 50, optional additional processing steps may be conducted to provide a third functionality or more to the mesostructure. Illustrative functionalization introduced at block 40 include: hydrophilicity, hydrophobicity, ion-conduction, adsorption selectivity, chemical reactivity, transport, electrical conduction, mechanical, optical, or opto-electronic properties.

For example, the first processing step includes acidic conditions, the second processing step includes alkaline conditions, and the third processing step includes predominantly non-aqueous conditions. In one embodiment, the first processing step forms a silica or organosilica framework, the second processing step incorporates hydrophilic aluminosilica moieties, and the third processing step incorporates acid groups.

It can be seen that it is possible to collectively optimize the first, second, and/or any subsequent sets of process conditions to obtain a combination of first, second, and subsequent functionalities. It is also possible to independently adjust the first, second, and subsequent sets of process conditions to control the first, second, and subsequent functional properties. For example, reversing the order of performing the first, second, and subsequent processing steps changes the first, second, and subsequent functional properties of the mesostructured material. It is also possible to activate the first functionality or second functionality with a later process steps.

Accordingly, the methods permit the functionality of the mesostructured material to be selectively tailored for specific characteristics or applications. For example, the mesostructured materials can be functionalized to include aluminum-containing moieties that occupy surface sites to enhance the hydrophilicity or reaction properties of the material.

The mesostructured materials can also be functionalized to include ion-conducting moieties. In one embodiment, the ion-conducting moieties are an acidic species, such as perfluorinated sulfonic acid, for proton-exchange membrane applications. In another embodiment, the ion-conducting moieties are lithium-containing species for battery applications.

In another embodiment, the mesostructured materials are functionalized to include one or more species that are adsorbed or occluded within the pores. In another embodiment, the adsorbed or occluded species includes water or triflic acid to enhance the ion-conductivity or barrier properties for proton-exchange membranes in fuel cells. For example, the aluminum-containing moieties, acidic species, and water or triflic acid can be optimized to enhance proton-conduction properties at temperatures greater than 80° C.

In another embodiment, the adsorbed or occluded species include optically responsive organic species, such as dyes, porphyrins, or conjugated polymers. In another embodiment, the pore-filling species includes nanoparticles, such as semi-conducting compounds ZnSe, ZnS, CdSe, CdS, GaN, GaP, InP, InGaP, GaAs, AlGaAs, metals, or oxides.

The invention may be better understood with reference to the accompanying examples, which are intended for purposes of illustration only and should not be construed as in any sense limiting the scope of the present invention as defined in the claims appended hereto.

Example 1

In order to demonstrate the functionality of the methods, a mesostructured block-copolymer/silica films with body-centered-cubic (Im$\bar{3}$m space group) structures were synthesized according to a procedure that has been described previously.

Typically, a solution containing 8.2 g tetraethoxysilane (TEOS) hydrolyzed in 0.007 g HCl, 3.6 g water, and 12 g ethanol was combined with a second solution containing 2.0 g poly(ethylene oxide)-poly(propylene oxide)-poly(ethylene oxide) triblock copolymer ($EO_{106}PO_{70}EO_{106}$, Pluronic F127®, BASF) dissolved in 20 g ethanol stirred for 2 h at room temperature, poured into a loosely-covered polystyrene Petri dish, and allowed to stand at a controlled temperature of 25° C. for approximately 3-5 days. During this time, the ethanol and water co-solvents evaporated and mesostructural ordering of the triblock copolymer and cross-linking of the silica precursor species occurred to yield free-standing transparent cubic mesostructured block-copolymer/silica films that were ~100 μm thick. The as-synthesized films were calcined to remove the structure-directing triblock copolymer species by heating at 1° C./min to 550° C. in air and holding at this temperature for 12 hours, which resulted in mesoporous silica films with thicknesses of ~60 μm.

Incorporation of aluminosilica moieties onto the interior mesopore surfaces was achieved by covalently grafting soluble aluminosilica precursor species in alkaline solution (pH ~11). Then, 2.0 g of the free-standing mesoporous silica films were placed in a polypropylene bottle containing 100 mL of 0.25 M solution of hydrolyzed $NaAlO_2$ and heated at 60° C. under gentle stirring for 12 hours. Samples with maximum aluminum content were reacted at 60° C. for 18 hours and shorter times led to lower amounts of aluminosilica incorporation. The aluminosilica-grafted mesoporous films were repeatedly washed with de-ionized water, followed by soaking in 1.0 M $H_2SO_4$ (aq) twice to ion-exchange $Na^+$ for $H^+$ ions from the films and rinsing in de-ionized water, until no further changes in pH were observed.

Perfluorosulfonic-acid (PFSA) species were covalently grafted onto the aluminosilica mesopore surfaces under non-aqueous conditions. 2.0 g of the ion-exchanged, mesoporous aluminosilica films were reacted with 1.0 g of 1,2,2-trifluoro-2-hydroxy-1-trifluoromethylethane-sulfonic-acid-beta-sultone (used as-received from Matrix Scientific, Columbia, S.C.) in 25 mL of dry (<0.005% $H_2O$) toluene at 110° C. for 4 hours. The perfluorosulfonic-acid-grafted aluminosilica films were subsequently washed with anhydrous toluene and dried at 100° C. in air. Finally, the PFSA-grafted mesoporous aluminosilica films were treated with aqueous triflic acid ($F_3CSO_3H$) solutions to fill the remaining mesopore volumes with $F_3CSO_3H$ species. Identical films were soaked at room temperature for 1 hour in solutions containing different concentrations of triflic acid from 0 M to 7.0 M (in 0.5 M increments) $F_3CSO_3H$ (aq) to obtain materials with a range of triflic-acid contents and to which proton conductivities were correlated. Identical PFSA- and triflic-acid-functionalization procedures were used for the mesoporous silica films that were not grafted first with aluminosilica species.

2D small-angle X-ray scattering (SAXS) patterns and transmission electron micrographs were collected to establish the degree of mesostructural ordering in the films. SAXS patterns were acquired using 1.54 Å Cu $K_\alpha$, radiation generated by a fine-focus (0.2 m) Rigaku rotating-angle generator and detected on a Bruker HI-STAR multiwire area detector. The free-standing silica films were positioned in the sample holder in transmission mode. 1D diffraction patterns were obtained from the 2D scattering data by 2θ integration. TEM samples were prepared by removing the mesostructured films from their substrates by using a razor blade or grinding the free-standing films into powders, forming slurries of the powders in ethanol, and dispersing them on a holey carbon grid. TEM images were collected on a JEOL 2010 microscope operating at 200 kV.

Elemental analyses were performed to quantify the bulk Si/Al ratios in the mesoporous aluminosilicas by using a TJA IRIS Inductively Coupled Plasma (ICP) spectrometer. The thermal stabilities of the various species within the mesopores of the functionalized perfluorosulfonic-acid-grafted aluminosilica films containing triflic acid were evaluated by thermogravimetric analyses (TGA), in combination with mass spectrometry of the effluent gases. The measurements (to ±1 wt %) were made using a Mettler TGA/sDTA851e Thermo-Gravimetric Analyzer coupled to a Blazers Thermostar Mass Spectrometer. The functionalized films were heated from 25° C. to 600° C. at a rate of 10° C./min under constant nitrogen gas flow of 50 L/min.

Solid-state nuclear magnetic resonance (NMR) spectroscopy was used to characterize the local structural and compositional environments of molecular species in the materials, especially those residing along the interior mesopore wall surfaces. NMR measurements were performed on identical functionalized films as those used for the proton conductivity measurements, with the exception that the films were gently ground to produce powders that were amenable for NMR investigation. Solid-state one-dimensional (1D) and two-dimensional (2D) NMR experiments were acquired on a Bruker AVANCE-300 NMR spectrometer, with a wide-bore 7 Tesla magnet, operating at 300.08 MHz, 282.34 MHz, 78.20 MHz, and 59.62 MHz, for $^1H$, $^{19}F$, $^{27}Al$, and $^{29}Si$, respectively. The measurements were performed under conditions of magic-angle spinning (MAS) using a 4-mm Bruker double-resonance broadband MAS probehead with variable temperature capabilities. This MAS probehead was equipped with a high-frequency splitter box to permit high-power proton decoupling during $^{19}F$ excitation and detection. 2D HETeronuclear chemical-shift CORrelation (HETCOR) NMR experiments differentiate dipole-dipole-coupled nuclei by spreading their chemical shifts into a 2D frequency map. This greatly enhances spectral resolution, thereby enabling the identification of adjacent (ca. 1 nm) molecular species. HETCOR NMR experiments were carried out under MAS conditions at 6 kHz and at low temperature (−30° C.) to reduce influences from molecular mobility, which can reduce dipolar coupling strengths. The low measurement temperature was selected, because cross-polarization was found to be possible between the aluminosilica and otherwise relatively mobile triflic acid species at temperatures ≤−30° C. For the 2D $^{29}Si\{^1H\}$ HETCOR spectra, a 4.8 µs $^1H$ 90° pulse, followed by a 2 ms contact time, were used for cross-polarization, and 512 acquisitions were collected with a 6 s recycle delay for 96 $t_1$ increments. For the 2D $^{27}Al\{^1H\}$ HETCOR spectra, a 4.8 µs $^1H$ 90° pulse, followed by a 1 ms contact time, were used for cross-polarization, and 896 acquisitions were collected with a 6 s recycle delay for 48 $t_1$ increments. In both the 2D $^{29}Si\{^{19}F\}$ and $^{27}Al\{^{19}F\}$ HETCOR experiments, a 5.5 µs $^{19}F$ 90° pulse was used. For the 2D $^{29}Si\{^{19}F\}$ HETCOR measurements, an 8 ms contact time with a 5 s recycle delay were used, and 5120 acquisitions were collected for 32 $t_1$ increments. For the 2D $^{27}Al\{^{19}F\}$ HETCOR measurement, a 5 ms contact time with a 5 s recycle delay were used, and 2048 acquisitions were collected for 32 $t_1$ increments. Contact times longer than 5 ms could not be used for the $^{27}Al\{^1H\}$ and $^{27}Al\{^{19}F\}$ HETCOR measurements, due to short $^{27}Al$ $T_{1\rho}$ relaxation times of several hundred microseconds. The $^1H$ and $^{29}Si$ chemical shifts were referenced to tetramethylsilane (TMS) using tetrakis(trimethylsilyl)silane [$(CH_3)_3Si]_4Si$ as a secondary standard, the $^{19}F$ chemical shifts were referenced to $CFCl_3$ using polytetrafluoroethylene [$(-CF_2-CF_2)_n$] as a secondary standard, and the $^{27}Al$ chemical shifts were referenced to an aqueous 0.5 M aluminum nitrate [$Al(NO_3)_3$] solution.

Quantitative solid-state $^{27}Al$ MAS spectra were acquired with sample spinning rates of 10 kHz and by applying 30° pulses to ensure correct relative quantification of the different $^{27}Al$ signals. A dense and known mass of aluminum nitride (AlN, 2 mg) was used as an internal standard to identify the aluminosilica species present and to establish their absolute populations. Quantitative $^{27}Al$ NMR measurements are challenging, due to the quadrupolar character of I=5/2 $^{27}Al$ nuclei, and interactions between their nuclear quadrupole moments and local electric field gradients. Compared to spin I=½ nuclei, such as $^1H$, $^{19}F$, $^{29}Si$, etc., under similar conditions of conventional MAS, anisotropic interactions of quadrupolar nuclei, such as $^{27}Al$, are only partially averaged, leading often to significant centerhand broadening from anisotropic second-order quadrupolar effects. Furthermore, because the electric field gradient in the vicinity of a given nucleus increases with decreasing symmetry of the nearby electronic environment, substantial additional broadening of $^{27}Al$ signals can result from species in locally distorted sites. Such spectral broadening may be so severe for quadrupolar nuclei in distorted environments, such as found in amorphous solids or at solid surfaces, that the signals become broadened into the baseline and resulting in high percentages of aluminum species being unobservable by $^{27}Al$ MAS NMR (so-called "NMR-invisible" aluminum species). $^{27}Al$ NMR signals were quantified by using AlN as an internal spin-counting standard and correlated with bulk elemental analyses to evaluate the fractions of NMR-visible and invisible $^{27}Al$ species.

Because both aluminosilica- and PFSA-grafted species compete for covalent attachment to surface silanol sites, their relative surface coverages were expressed and normalized relative to the number of surface silanol groups that were present after calcination of the as-synthesized films and before subsequent functionalization treatments. The absolute number of such silanol species were determined from quantitative $^{29}Si$ MAS NMR spectra shown in FIG. 9, which yielded signals at −102 ppm and −110 ppm, corresponding to $Q^3$ silanol moieties and fully condensed $Q^4$ framework silica species, respectively. The relative integrated intensities of these $^{29}$Si MAS signals remained unchanged within ±10% following each of the alkaline, non-aqueous, and acid functionalization treatments.

Bulk proton conductivity in the temperature range 140-200° C. was the principal macroscopic property criterion used to optimize the various functionalization steps. Proton conductivities were measured by AC impedance spectroscopy using a Solartron 1260 Impedance/Gain-Phase Analyzer over the frequency range 0.1 Hz to 1 MHz with an AC amplitude of 10 mV. The ohmic resistances of the films were extracted from Nyquist impedance plots generated using the ZPlot/ZView software package. For the measurements, the films were placed identically in a Teflon® cell using platinum foil as a back contact electrode. The proton conductivity of each film was measured as a function of temperature at a selected and well controlled relative humidity (RH). The measurement cell containing a given film was placed in a stainless-steel environmental chamber, along with a known quantity of de-ionized water that depended upon the amount required to yield the desired relative humidity (e.g., 50% or other) at each temperature. Each film was allowed to equilibrate for at least 60 min at each temperature and humidity prior to measurement of its proton conductivity.

It was shown that novel acid-functionalized cubic mesoporous aluminosilica films can be synthesized using a versatile 'sequential processing' protocol that allows the independent adjustment of the conditions under which the various components are incorporated. Free-standing mesoporous silica films resulted from cooperative self-assembly of $EO_{106}PO_{70}EO_{106}$ triblock-copolymer species and a network-forming inorganic precursor species (hydrolyzed silica) under acidic (pH 1.5) conditions during evaporation of volatile solvents (ethanol and water). The structure-directing block-copolymer species were subsequently removed from the mesostructured film through solvent extraction or oxidation, leaving behind mesoporous silica films.

To evaluate the synthesis conditions used in this example, small-angle X-ray scattering results and transmission electron micrographs as shown in FIG. 10A and FIG. 10B established that the mesoporous silica films were three-dimensionally ordered with a body-centered-cubic (Im $\overline{3}$ m) structure and a $d_{110}$ spacing of 11.7 nm.

Analyses of nitrogen adsorption isotherms as seen in FIG. 11 revealed that the films had mesopores with mean diameters of 8.5 nm and surface areas of ~400 $m^2$/g that could be subsequently functionalized.

Hydrophilic moieties were introduced along the interior mesopore surfaces through post-synthetic grafting of aluminosilica species under alkaline (pH ~11) solution conditions. The presence of aluminosilica surface sites in the mesopores was expected to improve significantly water retention of the materials at elevated temperatures (100-200° C.). The incorporation of co-condensed aluminosilica species during formation of cubic mesostructured films was not possible under the conditions used, which resulted in the precipitation of separate silica and alumina particles and poor film ordering. In contrast, superior control over mesostructural framework order, film quality, and mechanical/hydrothermal stabilities was achieved by post-synthetic grafting of hydrophilic aluminosilica species at desirable surface sites in cubic mesoporous silica films. Further functionalization of the hydrophilic mesopore surfaces by covalent grafting of perfluorosulfonic-acid species under non-aqueous conditions and subsequent pore-backfilling with aqueous triflic acid ($F_3CSO_3H$) solutions yielded a robust film with stable proton conductivity properties at temperatures well above 100° C. By understanding and controlling the compositions, structures, and interfacial interactions of molecular species within the mesoporous films, their macroscopic ion-conduction properties can be enhanced. Such insights yield key molecular design and processing criteria that allow the incorporation and collective optimization of multiple functional properties, even those that may rely on incompatible synthesis conditions.

Figure 2:
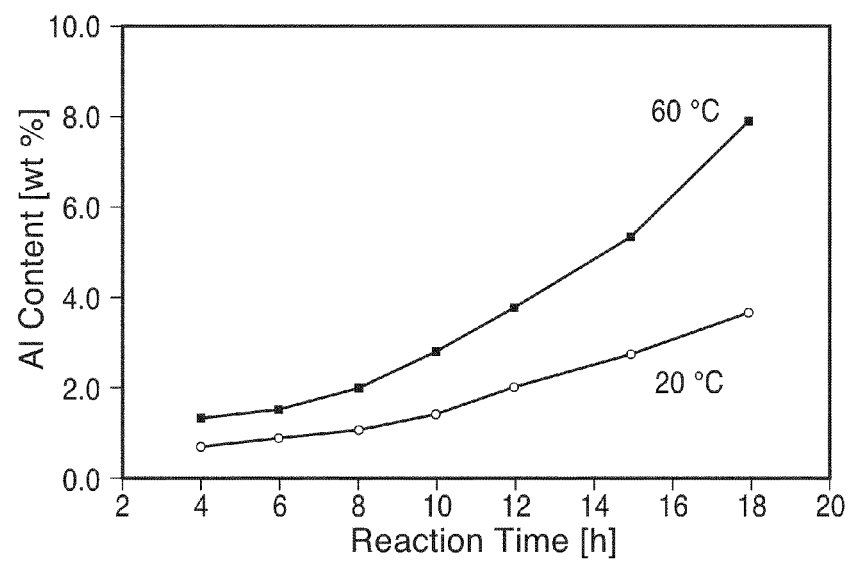
FIG. 2 is a graph of the aluminum contents in aluminosilica-functionalized cubic mesoporous films shown as functions of reaction time and temperature in alkaline (pH ~11) alumina grafting solutions.

The extent of incorporation of hydrophilic aluminosilica moieties onto the interior mesopore surfaces depends on temperature, composition (e.g., pH) of the alkaline grafting solution, and the time it is allowed to contact the mesoporous silica films. Due to the alkaline conditions of the grafting solution, Si—O—Si bonds undergo partial cleavage, thus promoting inclusion of hydrolyzed aluminum hydroxide species at the otherwise siliceous mesopore surfaces. For example, FIG. 2 shows elemental analysis results for cubic mesoporous silica films exposed to the same alkaline (pH ~11) alumina solution, as functions of reaction time at 20° C. and 60° C. At higher temperatures and longer reaction times, higher aluminosilica grafting densities are achieved, up to 7.8 wt % Al, after 18 hours at 60° C. without significant deterioration of the cubic mesostructural ordering of the films. Still higher aluminosilica concentrations can be incorporated at longer reaction times (>18 hours) and temperatures above 60° C., but only at the expense of mesostructural ordering, which leads to a loss in the mechanical and structural integrities of the films.

Bulk aluminosilica concentrations in the mesoporous films were determined by elemental analysis after each subsequent step of the 'sequential functionalization' protocol. Table 1 shows elemental analysis results for the mesostructured silica film, aluminosilica-only film, PFSA-grafted aluminosilica film, and PFSA-grafted aluminosilica film containing 8 wt % triflic acid backfilled into the mesopores, from which bulk molar Si/Al ratios were determined for each sample. All of the films were prepared from the same cubic mesoporous silica film template and exposed to identical aluminosilica- and PFSA-grafting solutions, as appropriate. Incorporation of aluminosilica into the silica films for 12 hours at 60° C. yielded material with a Si/Al molar ratio of 15.6±0.5 (3.7 wt % Al). During the subsequent grafting of the perfluorosulfonic-acid species, ~8% of the bulk aluminum in the aluminosilica-grafted silica film was lost to the perfluorosulfonic-acid grafting solution, resulting in a Si/Al molar ratio of 16.8±0.4 (3.5 wt % Al) in the functionalized film. Dissolution of the small amount of aluminosilica resulted from cleavage of some Si—O—Al bonds, due to interactions with the perfluorosulfonic-acid species under the relatively high temperature (110° C.) PFSA-grafting conditions used. By comparison, no significant loss of aluminum (Si/Al=16.9±0.2) was observed during the subsequent backfilling of the mesopores with 4 M triflic acid at room temperature. The resulting functionalized film contained 8 wt % triflic acid within the mesopores.

Figure 3A:
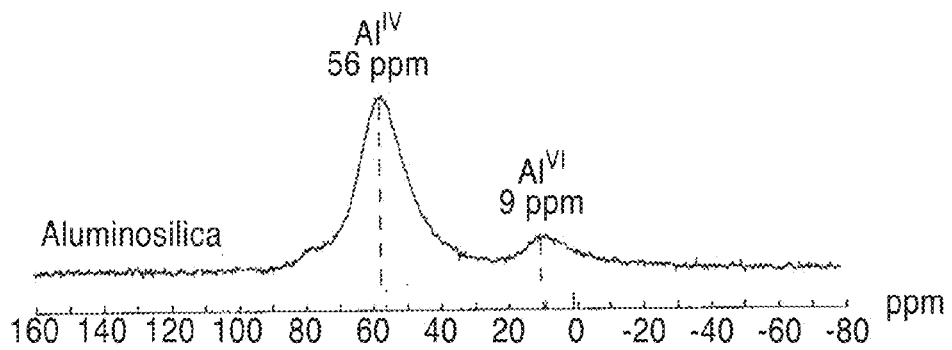
FIG. 3A is a solid-state single-pulse $^{27}$Al MAS NMR spectrum of cubic mesoporous aluminosilica (3.7 w % Al).
Figure 3B:
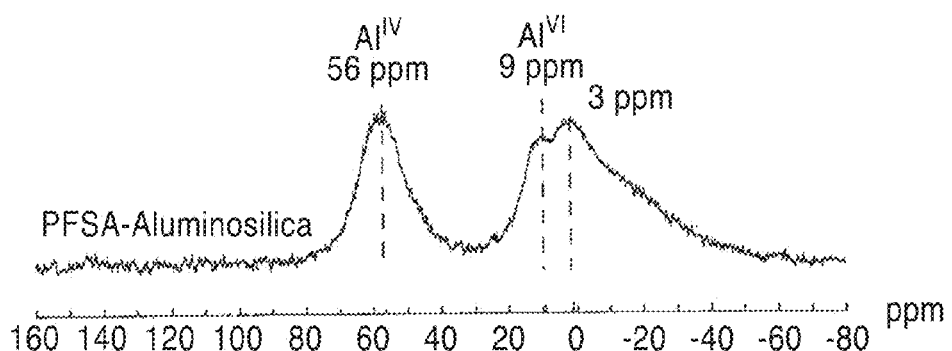
FIG. 3B is a solid-state single-pulse $^{27}$Al MAS NMR spectrum of cubic mesoporous PFSA-grafted (5 wt % PFSA) aluminosilica (3.5 wt % Al).
Figure 3C:
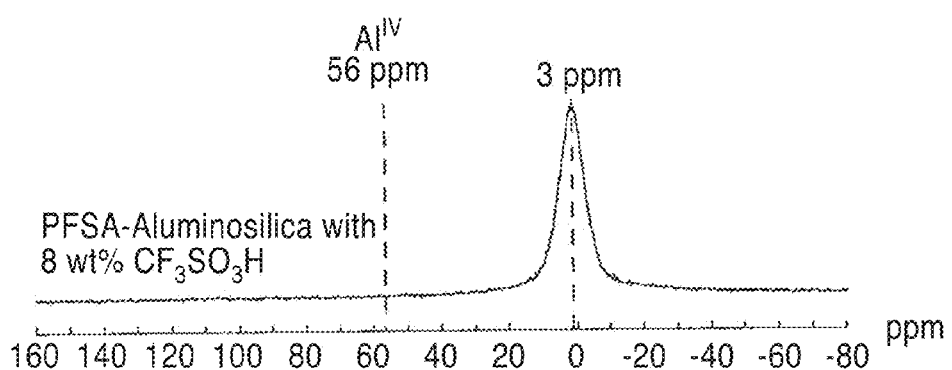
FIG. 3C is a solid-state single-pulse $^{27}$Al MAS NMR spectrum of cubic mesoporous PFSA-grafted (5 wt % PFSA) aluminosilica (3.5 wt % Al) containing wt % F$_3$CSO$_3$H acid backfilled into the mesopores. The relative integrated intensities of the peaks in the spectra correspond to the relative populations of the different four- and six-coordinate Al species shown in Table 1.

Quantitative single-pulse $^{27}$Al MAS NMR spectra of the functionalized membranes are consistent with the bulk elemental analyses and provide insight into the coordination and relative and absolute concentrations of the different types of aluminosilica moieties in the films. For example, the $^{27}$Al MAS NMR spectrum that is seen in FIG. 3A for a powder obtained from a aluminosilica-functionalized film containing 3.7 wt % Al (Si/Al=15.6) shows two $^{27}$Al signals, whose chemical-shifts of 56 ppm and 9 ppm are consistent with four- and six-coordinate aluminosilica species, respectively. In addition, integration of the peak areas establishes that 92% of the aluminosilica sties are four-coordinated (Table 1). It is noteworthy that in FIG. 3A, over 90% of the total aluminum atoms in the material, as determined by elemental analysis, are accounted for in the $^{27}$Al MAS spectrum by using a known mass of AlN as an internal spin-counting standard. Similar quantitative analysis of the $^{27}$Al MAS NMR spectrum (FIG. 3B) for the PFSA-grafted (5 wt % PFSA) mesoporous aluminosilica film (3.5 wt % Al), prior to backfilling with triflic acid, establishes that the perfluorosulfonic-acid functionalization step converts 53% of the framework aluminosilica species from four-coordinate $Al^{IV}$ to six-coordinate $Al^{VI}$ species. Furthermore, there are two distinct six-coordinate alminosilica species, corresponding to the peaks at 9 ppm and 3 ppm. This trend continues upon incorporation of triflic acid into the mesopores of otherwise identical PFSA- and aluminosilica-grafted mesoporous films. The $^{27}$Al MAS NMR spectrum in FIG. 3C acquired for the PFSA-grafted aluminosilica film containing 8 wt % triflic acid back-filling the mesopores contains a dominant (99%) $^{27}$Al signal at 3 ppm corresponding to six-coordinate $Al^{VI}$ species, while the $^{27}$Al peak at 56 ppm associated with four-coordinate $Al^{IV}$ moieties has almost completely disappeared, along with the six-coordinate aluminosilica peak at 9 ppm. The increase in coordination of the surface aluminosilica moieties is due to strong interactions with adsorbed water and triflic acid species, as will be shown and discussed in detail below.

Molecular Surface Interactions. More detailed information on the local structures and interactions of the various molecular species present in PFSA-grafted mesoporous aluminosilica films with triflic acid-filled pores can be established through the use of 2D HETCOR NMR experiments. For the materials of interest here, dipolar couplings between $^1$H or $^{19}$F and $^{29}$Si or $^{27}$Al nuclei can be used to distinguish protonated or fluorinated species (e.g., water, perfluorosulfonic acid, and triflic acid) that are in close molecular (ca. 1 nm) proximities to specific silicon or aluminum moieties associated with the inorganic framework. By this method, unambiguous information is obtained on local compositions and molecular-level structures in acid-functionalized mesoporous aluminosilica films, particularly with respect to surface grafting and adsorption sites in the mesopore channels.

Solid-state 2D $^{29}$Si{$^1$H} HETCOR results establish correlations between various proton moieties (e.g., adsorbed water and surface hydroxyl groups) and framework $^{29}$Si sites in functionalized mesoporous films. FIG. 4A shows the 2D $^{29}$Si{$^1$H} HETCOR spectrum acquired at –30° C. of PFSA-grafted (5 wt % PFSA) cubic mesoporous aluminosilica (3.5 wt % Al) containing 8 wt % triflic acid back-filling the mesopores. Separately acquired quantitative single-pulse $^{29}$Si and $^1$H MAS spectra are plotted along the corresponding axes of the 2D HETCOR contour plot, so that all of the resonances are accounted for, even if they do not contribute signal intensity correlations in the 2D spectrum. The 1D $^{29}$Si MAS spectrum along the horizontal axis in FIG. 4A confirms the presence of two broad overlapping peaks, whose chemical-shifts of –102 ppm and –110 ppm are consistent with partially polymerized $Q^3$ and fully cross-linked $Q^4$ $^{29}$Si sites in the silica framework. The peak at –102 ppm is expected also to have an additional contribution from fully cross-linked $^{29}$Si sites that have one $^{27}$Al nearest neighbor, referred to here as $Q^4$ (1 Al) sites. The single-pulse $^1$H MAS spectrum displayed along the vertical axis in FIG. 4A shows two broad peaks, corresponding to surface hydroxyl groups (1.6 ppm, 2 ppm full-width-half-maximum, fwhm) and adsorbed water (4.0 ppm, 3 ppm fwhm). The broad nature of the overlapping peaks is attributed to strong homonuclear $^1$H-$^1$H dipolar couplings. The $^{29}$Si{$^1$H} HETCOR contour plot shown in FIG. 4A shows strong 2D signal intensity at 1.6 ppm in the $^1$H dimension and –102 ppm in the $^{29}$Si dimension, which is ascribed to hydroxyl groups directly bonded to $Q^3$ $^{29}$Si sites. In addition, 2D signal intensity at 4.0 ppm in the $^1$H dimension and –102 ppm in the $^{29}$Si dimension can arise from polarization transfer between adsorbed water protons and either hydrogen bonded $Q^3$ $^{29}$Si silanol species or $Q^4$(1 Al) $^{29}$Si moieties adjacent to neighboring aluminum grafting sites.

A similar solid-state 2D $^{27}$Al{$^1$H} HETCOR spectrum was also acquired at –30° C. for the same PFSA-grafted (5 wt % PFSA) cubic mesoporous aluminosilica (3.5 wt % Al) with 8 wt % triflic acid establishes that strong interactions exist between protonated species and distinct framework $^{27}$Al aluminosilica sites. A separately acquired single-pulse $^{27}$Al MAS spectrum, along with the same $^1$H MAS spectrum as shown in FIG. 4A, are displayed along the corresponding axes of the 2D $^{27}$Al{$^1$H} HETCOR contour plot in FIG. 4B. The single-pulse $^{27}$Al MAS spectrum reveals a sharp dominant peak at 3 ppm and with only a hint of a very weak peak at 56 ppm, which are attributed to predominant (99%) six-coordinate and virtually absent (1%) four-coordinate $^{27}$Al species, respectively [Table 1, bottom]. Notably, the 2D contour plot of the $^{27}$Al{$^1$H} HETCOR spectrum contains only a single 2D intensity correlation at 3 ppm in the $^{27}$Al dimension and 4.0 ppm in the $^1$H dimension. This strong 2D signal intensity originates from strong dipole-dipole couplings between the six-coordinate framework $^{27}$Al aluminosilica species and spatially proximate protons of adsorbed water molecules. The strong interaction between adsorbed water and the grafted aluminosilica surface species reflects the enhanced hydrophilicity of the mesopores and accounts for the higher water retention properties of the functionalized material. A schematic diagram consistent with the above (and following experimental measurements) is shown in FIG. 4C, depicting the various surface-grafted aluminosilica, surface-grafted perfluorinated-sulfonic acid, and adsorbed triflic acid species in a single cubic mesopore.

Figure 4C:
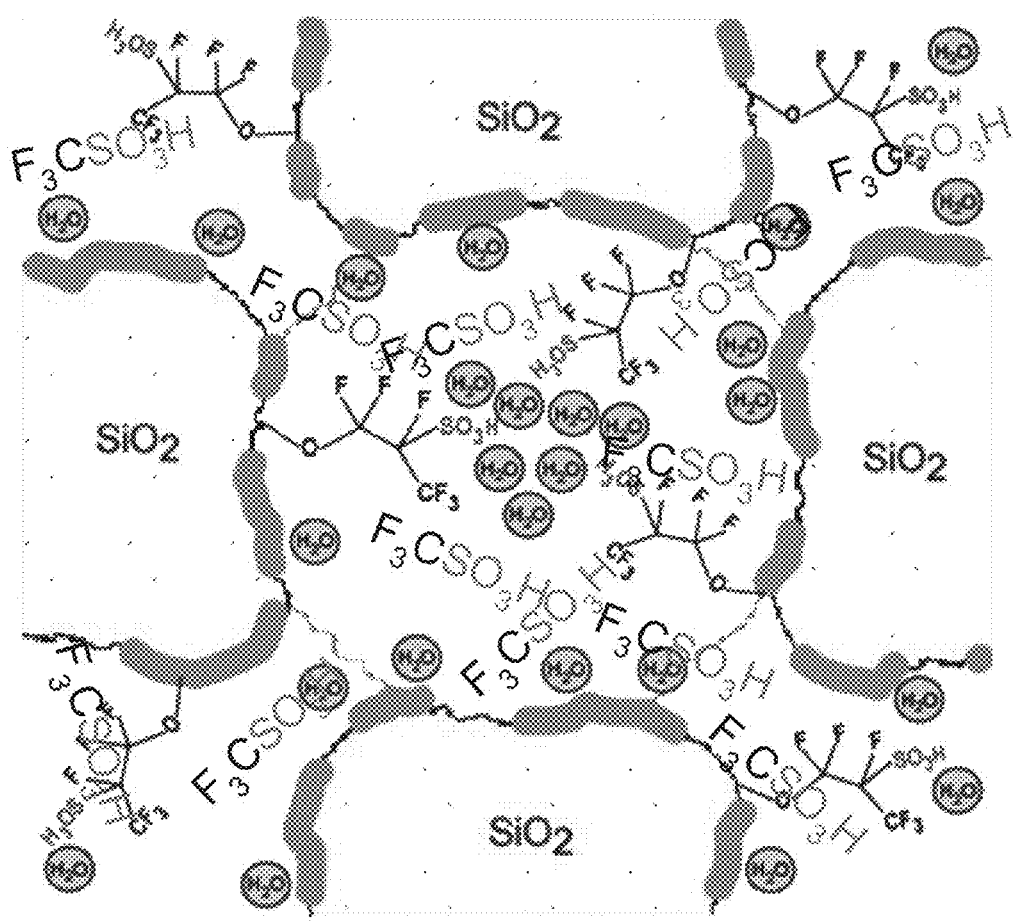
FIG. 4C is a schematic diagram of mesopore structure consistent with experimental results, showing surface-grafted aluminosilica, surface-grafted perfluorinated-sulfonic acid, and adsorbed triflic acid species in a single cubic silica mesopore.

Analogous $^{29}$Si{$^{19}$F} and $^{27}$Al{$^{19}$F} HETCOR measurements to those shown in FIG. 4A and FIG. 4B provide important additional insights into interactions between the proton-conducting moieties, e.g., the covalently grafted PFSA and adsorbed triflic acid species, and framework silica and aluminosilica sites in the functionalized films.

Specifically, $^{29}$Si{$^{19}$F} and $^{27}$Al{$^{19}$F} HETCOR experiments were conducted at –30° C. on powders prepared from PFSA-grafted (5 wt % PFSA) cubic mesoporous aluminosilica (3.5 wt % Al) films, with and without triflic acid back-filling the mesopores, to elucidate surface grafting/adsorption sites of the perfluorosulfonic-acid and triflic acid species. FIG. 5A shows the corresponding 2D $^{29}$Si{$^{19}$F} HETCOR spectrum, together with a separately acquired single-pulse $^{29}$Si MAS spectrum along the horizontal axis and a single-pulse $^{19}$F MAS spectrum along the vertical axis; a portion of the spectrum has been enlarged so that all of all peaks are visible. The three $^{19}$F peaks at –169 ppm, –153 ppm, and –74 ppm have isotropic chemical shifts and integrated-area ratios that are consistent with the relative stoichiometries of the fluorine moieties of grafted perfluorosulfonic acid species. The narrow peak at –79 ppm in the $^{19}$F MAS spectrum is assigned to the methyl fluorine atoms of the triflic acid ($F_3CSO_3H$) species. An identical single-pulse $^{19}$F MAS spectrum is obtained for the PFSA-grafted cubic mesoporous aluminosilica film material prior to triflic acid pore-backfilling, except that the narrow peak at –79 ppm is not present in FIG. 12.

In the 2D $^{29}$Si{$^{19}$F} HETCOR spectra for PFSA-grafted cubic mesoporous aluminosilica film materials with shown in FIG. 5A and without triflic acid, seen in FIG. 12, backfilling the mesopores, correlated 2D signal intensity is observed at −153 ppm in the $^{19}$F dimension and −115 ppm in the $^{29}$Si dimension, providing unambiguous confirmation that the perfluorosulfonic-acid species are grafted through their —CF$_2$— groups to the mesopore silica surfaces, in the same configuration as suggested by Alvaro et al. Furthermore, the up-field-shifted $^{29}$Si signal (−115 ppm) associated with this intensity correlation indicates that the —CF$_2$— perfluorosulfonic-acid moieties interact strongly with Q$^3$ $^{29}$Si grafting sites, shifting the $^{29}$Si resonance up-field well beyond the ca. −100 ppm position typical for framework Q$^3$ $^{29}$Si sites.

Density functional theory (DFT) calculations of NMR parameters on model [O—Si(OH)$_3$]$_3$Si—O—X clusters (X=H or CF$_3$) confirm that large upfield $^{29}$Si shifts result from interactions between —CF$_2$— perfluorosulfonic-acid moieties and Q$^4$(1 C) $^{29}$Si sites (formerly Q$^3$ silanols) to which they are expected to be directly bonded. DFT calculations show that the grafting of PFSA species on such Q$^4$(1 C) $^{29}$Si sites is expected to result in $^{29}$Si NMR signals that are shifted upfield by ca. −11 to −14 ppm from hydroxylated Q$^3$ $_{29}$Si resonance at −102 ppm. Calculated DFT cluster structures furthermore suggest that, on average, the minimum distances between the —CF$_2$— moieties and the Q$^4$(1 C) $^{29}$Si grafting sites are typically shorter (ca. 0.30 nm) than the distances between these fluorine atoms and nearby non-PFSA-grafted Q$^4$ silicon atoms (ca. 0.35-0.40 nm). These calculations show that PFSA species interacting with the other nearby $^{29}$Si Q$^4$ sites are expected to induce much smaller $^{29}$Si shifts, ca. 1 ppm, compared to typical Q$^4$ signals at ca. −110 ppm. These results are consistent with the 2D $^{29}$Si{$^{19}$F} HETCOR spectrum seen in FIG. 5A, which shows correlated intensity between the $^{19}$F signal at −153 ppm from the PFSA —CF$_2$— species and a $^{29}$Si signal at −115 ppm, which is thus assignable to PFSA-grafted Q$^4$(1 C) $^{29}$Si sites, whose resonance is shifted by ca. −13 ppm due to the strong interactions with the —CF$_2$— groups.

As evident in FIG. 5A, the $^{29}$Si{$^{19}$F} HETCOR spectrum for the PFSA-grafted cubic mesoporous aluminosilica film material containing 8 wt % triflic acid also displays strong correlated 2D signal intensity at −79 ppm in the $^{19}$F dimension and −102 ppm in the $^{29}$Si dimension, corresponding to triflic acid species interacting with surface Q$^3$ $^{29}$Si sites. The high mobility at room temperature of the —CF$_3$ group in the triflic acid species required that the sample be cooled to −30° C. before magnetization transfer was possible between the $^{19}$F nuclei and $^{29}$Si species in the inorganic framework. This interaction presumably occurs through either hydrogen bonding between the hydroxyl group of a Q$^3$ site and the triflic acid, or adsorption of the triflic acid species on a neighboring aluminum atom of a Q$^4$(1 Al) $^{29}$Si site, leading to close spatial proximity of the triflic acid —CF$_3$ fluorine atoms and $^{29}$Si nuclei of the Q$^4$(1 Al) mesopore surface sites. These results are consistent with weaker interactions between the adsorbed and more mobile triflic acid species at surface sites, compared to the covalently grafted PFSA moieties.

The 2D $^{29}$Si{$^{19}$F} HETCOR results shown in FIG. 5A are corroborated by the 2D $^{27}$Al{$^{19}$F} HETCOR spectrum shown in FIG. 5B for the same PFSA-grafted (5 wt % PFSA) cubic mesoporous aluminosilica (3.5 wt % Al) film material containing 8 wt % triflic acid; namely, that the perfluorosulfonic acid species are only grafted to the mesopore surface through Q$^4$(1 C) silicon sites (formerly Q$^3$ silanol moieties) and the triflic acid species adsorb to framework aluminum sites to yield six-coordinate Al species.

The 2D $^{27}$Al{$^{19}$F} HETCOR contour plot in FIG. 5B shows one 2D signal intensity correlation at −79 ppm in the $^{19}$F dimension and 3 ppm in the $^{27}$Al dimension, corresponding to interactions between the fluorine atoms of adsorbed triflic acid moieties and six-coordinate aluminosilica $^{27}$Al mesopore surface sites. As in the $^{29}$Si{$^{19}$F} HETCOR experiment, the $^{27}$Al{$^{19}$F} HETCOR measurement was also conducted at −30° C. to reduce the mobility of the triflic acid fluorine atoms and allow for cross-polarization. The —CF$_2$— fluorine atoms of the grafted perfluorosulfonic acid species are capable of cross-polarizing to $^{29}$Si nuclei associated with the aluminosilica mesopore surface moieties at room temperature, consistent with these functional groups being covalently bonded to the mesopore walls and thus less mobile. In contrast, the triflic acid molecules require temperatures ≤−30° C. to slow their mobilities sufficiently that their dipolar couplings to $^{27}$Al aluminosilica surface sites are not averaged away. Consequently, at relevant PEM fuel cell operating temperatures (T>60° C.), the triflic acid species are highly mobile and contribute to the enhanced conductivity of ions within the backfilled-mesopore channels of PFSA-functionalized films, while the PFSA moieties remain anchored to the mesopore walls.

In contrast to the 2D $^{29}$Si{$^{19}$F} HETCOR spectrum shown in FIG. 5A discussed above, the absence of any signal intensity in the 2D $^{27}$Al{$^{19}$F} HETCOR spectrum of FIG. 5B at any of the $^{19}$F chemical-shifts corresponding to the perfluorosulfonic-acid (non-triflic acid) species (−169 ppm, −153 ppm, or −74 ppm) establishes unambiguously that the grafted perfluorosulfonic-acid species are only bonded to the mesopore surfaces at silica-rich sites as seen in FIG. 4C.

Optimization of mesopore functionalities was then evaluated. The selective grafting of perfluorosulfonic-acid species onto surface silica sites suggests that the proton conductivity properties at elevated temperatures can be improved by collectively optimizing the aluminosilica and PFSA grafting densities on the interior mesopore surfaces. As discussed previously with FIG. 2, maximum hydrophilicity is obtained at the highest aluminosilica surface coverages. However, in this case the number of surface silanol sites available for PFSA grafting are significantly reduced (and mesostructural ordering potentially diminished), leading to relatively low proton conductivities at all temperatures. Similarly, high loadings of proton-conducting PFSA species are achieved with high surface silanol concentrations and low aluminosilica coverages, although this leads to significantly lower material hydrophilicity and water retention and thus relatively low proton conductivities at elevated temperatures. Consequently, it is necessary to optimize the mesopore surface compositions to allow for a high concentration of grafted perfluorosulfonic-acid species, while maintaining highly hydrophilic surface environments within the mesopore channels.

Temperature-dependent proton conductivities were measured and compared for mesoporous films, following different functionalization treatments designed to optimize aluminosilica and PFSA concentrations (first in the absence of additional triflic acid in the mesopores.) These films included calcined cubic mesoporous silica, cubic mesoporous aluminosilica with 3.5 wt % Al (corresponding to ca. 35% silanol coverage, see Experimental section), and cubic mesoporous aluminosilica with a maximum aluminosilica surface density of 7.8 wt % Al (corresponding to a ca. 85% silanol coverage). (Optimization of non-covalently grafted triflic acid concentrations in the mesopores is discussed separately below.) After PFSA grafting under identical conditions, each of these films yielded loadings of 8 wt %, 5 wt %, and 1 wt % PFSA, corresponding to silanol coverages of approximately 90%, 55%, and 10%, respectively.

As discussed above with FIG. 2, silanol coverages by aluminosilica species above 85% are possible and higher aluminosilica concentrations achievable, though with degradation of mesostructural ordering in the film. Additionally, the alkaline-soluble alumina species compete with non-aqueous-soluble PFSA species for surface silanol groups in the sequential grafting treatments. Consequently, increased aluminosilica surface densities can be achieved in the mesopore channels, though at the expense of reducing the perfluorosulfonic-acid surface concentrations. Thus, the two must be optimized together to maximize the proton conductivity properties of the functionalized film materials at elevated temperatures.

For example, FIG. 6A shows plots of proton conductivity, measured as functions of temperature at 50% relative humidity, for three otherwise identical cubic mesoporous silica films that were functionalized with different aluminosilica and perfluorinated-sulfonic-acid surface-grafting densities. If no hydrophilic surface aluminosilica species are incorporated (0 wt % Al), a maximum amount of PFSA species (8 wt %) can be grafted onto the silica mesopore surfaces, leading to maximum proton conductivities of ca. $5.7 \times 10^{-3}$ S/cm at 40° C. as shown in FIG. 6A. Above this temperature, the conductivity values diminish rapidly, consistent with the low water retention of the non-aluminosilica-containing materials that leads to low proton mobilities. In the other limit, for a maximum amount of hydrophilic aluminosilica (7.8 wt % Al) species incorporated onto the mesopore surfaces and the remaining silanol groups grafted with PFSA (1 wt %), maximum proton conductivities of approximately $4.5 \times 10^{-2}$ S/cm were measured at 60° C. (FIG. 6A). This lower value reflects the lower concentration of proton-conducting moieties present, as a result of competitive consumption of surface silanol species by the aluminosilica sites. At higher temperatures, significantly lower conductivities are also observed, with both PFSA-only-grafted (8 wt % PFSA) silica and high aluminosilica (7.8 Al wt %, 1 wt % PFSA) cubic mesoporous films displaying comparable conductivity values between 60-180° C. For functionalized cubic mesoporous films containing aluminosilica and PFSA loadings between these two limits, proton conductivities were measured and could be enhanced at intermediate levels of the two functional components.

By balancing the need for both high hydrophilicity and strong acidity, aluminosilica and perfluorosulfonic-acid surface-grafting densities were co-optimized in functionalized films, according to their temperature-dependent proton-conduction properties. Specifically, a cubic mesoporous film with aluminosilica and PFSA contents of 3.5 wt % Al and 5 wt % PFSA (ca. 35% and 55% silanol coverages, respectively) yielded the highest proton conductivity values at all measured temperatures as see in FIG. 6A. Maximum conductivity values of ca. $7.7 \times 10^{-2}$ S/cm were measured over the range 80-100° C. and persisted above $6.0 \times 10^{-2}$ S/cm up to approximately 140° C. Optimization of the bulk proton conductivities of the functionalized films to this extent was directly enabled by understanding the competitive molecular interactions at the various hydrophilic- and acidic-grafting sites within the mesopore channels and at their heterogeneous interfaces.

Proton conductivities of the perfluorosulfonic-acid functionalized cubic mesoporous aluminosilica films are functions of temperature and relative humidity, as well as the concentration of fluorosulfonic-acid species within the mesopore channels. While grafted perfluorosulfonic-acid moieties allow for proton conduction along the mesopore surfaces, additional proton conduction capacity through the membranes can be produced by increasing the concentration of fluorosulfonic-acid moieties in the films by filling the remaining mesopore volumes with triflic acid ($F_3CSO_3H$). This can be achieved by contacting the mesoporous films (silica, aluminosilica, and/or PFSA-grafted) with an aqueous solution of triflic acid, the concentration of which can be increased to increase the $F_3CSO_3H$-loading in the mesopores. While one might think that proton conductivity could be maximized by incorporating the highest concentrations of triflic acid into the mesopores, this turns out not to be the case. Rather, intermediate pore-volume concentrations of triflic acid were found to yield highest proton conductivities in PFSA-grafted cubic mesoporous aluminosilica films, reflecting a new and different underlying optimization criterion to the competitive silanol grafting constraints discussed above.

Similarly, the influence of adsorbed triflic acid concentrations on the proton conductivity properties of otherwise identical perfluorosulfonic-acid- and aluminosilica-grafted mesoporous silica films were optimized in accordance with the molecular insights provided by solid-state 2D NMR [FIG. 5]. In FIG. 6B, proton conductivity is plotted as a function of mesopore-filling triflic acid concentrations in 5 wt % PFSA- and 3.5 wt % Al aluminosilica-grafted cubic mesoporous silica films. Functionalized films soaked in 0 M, 2 M, 4 M, and 6 M aqueous triflic acid solutions were measured to contain 0 wt %, 4 wt %, 8 wt %, and 11 wt % triflic acid, respectively, in the mesopores after air-drying. At low triflic acid concentrations, low conductivity values result, (e.g., $1.0 \times 10^{-2}$ S/cm for 4 wt % $F_3CSO_3H$), due to inherently low proton concentrations in the mesoschannels. As the concentration of triflic acid in the mesopores is increased (by contact with more concentrated $F_3CSO_3H$ solutions), the proton conductivity was measured to increase to a maximum value of $1.5 \times 10^{-2}$ S/cm for 8 wt % triflic acid (4 M $F_3CSO_3H$). At still higher concentrations of triflic acid, however, significantly lower proton conductivities were observed. Importantly, these measurements are additionally correlated with the concentration of co-existing water in the mesopores, which fills the remaining free mesopore volume and which decreased steadily at higher triflic acid loadings. Separate TGA/mass spectrometry measurements establish that, at 20° C., identical films with 4 wt %, 8 wt %, and 11 wt % $F_3CSO_3H$ in the mesopores possess co-adsorbed water loadings of 25 wt %, 22 wt %, and 18 wt % $H_2O$, respectively. The existence of an optimal mesopore $F_3CSO_3H$ concentration for which maximum proton conductivity is observed appears to be correlated with competitive incorporation of triflic acid species and water in the mesopore channels.

The effects of the different optimization criteria identified and discussed above can be clearly seen in FIG. 6C, where the macroscopic proton conductivities of differently functionalized films are plotted as functions of temperature. It is particularly interesting to compare the different proton conductivity values obtained for materials optimized with respect to individual versus collective criteria (e.g., aluminosilica, PFSA, and/or triflic acid loadings). For example, a cubic mesoporous silica film grafted with aluminosilica (3.7 wt % Al) and no perfluorosulfonic acid species displays negligible proton conductivity. By comparison, a PFSA-grafted aluminosilica film (5 wt % PFSA, 3.5 wt % Al) with no triflic acid back-filling the mesopores exhibits stable proton conductivity values of $4$-$7 \times 10^{-3}$ S/cm between 20-180° C. The introduction of 4 wt % triflic acid into the mesopores of an otherwise identical PFSA-grafted aluminosilica film (FIG. 6C) increases the total acid concentration, leading to two-fold higher proton conductivity in this film, with a maximum value of $1.3 \times 10^{-2}$ S/cm at 80-100° C. This trend of increased triflic acid concentrations in the mesopores leading to higher proton conductivities in otherwise identical PFSA-functionalized cubic mesoporous aluminosilica films continues up to triflic acid loadings of 8 wt % (FIG. 6C). Over the temperature range 20-160° C., high and stable proton conductivity values (up to $1.8 \times 10^{-2}$ S/cm) were measured for a PFSA-grafted aluminosilica film containing 8 wt % triflic acid backfilling the mesopores. At still higher triflic acid loadings (>8 wt %, for the films examined here), lower proton conductivities resulted. As shown in FIG. 6C for an otherwise identical film containing 11 wt % triflic acid, significantly lower conductivities were measured over the temperature range 20° C. to 180° C. As discussed above, these results are consistent with initially higher concentrations of triflic acid contributing greater numbers of protons in the mesoscale channels, with the balance of the mesopore volume available to adsorbed/occluded water that facilitates mobility of the ion species. However, as the concentration of triflic acid increases, and along with it the concentration of protons, the amount of residual mesopore volume available to water diminishes, eventually to a point (>8 wt %) where proton mobility and thus proton conductivity also begin to diminish. Thus, the existence of optimal concentrations of functional species in the mesoporous films for which maximum proton conductivity is observed is likely a consequence of the competing effects of higher densities of strong acid sites in the mesopore channels being offset by reduced local hydration of the triflic acid species and resulting increased viscous resistance to proton conduction.

Local dehydration and interruption of ion-conducting channel connectivities are similarly thought to account for the reduced proton conductivities of wholly polymeric materials at elevated temperatures. For comparison, proton conductivity values as functions of relative humidity (RH) at three different temperatures (60° C., 120° C., or 160° C.) under otherwise identical measurement conditions are shown in FIG. 7 for the collectively optimized PFSA-grafted (5 wt % PFSA) cubic mesoporous aluminosilica (3.5 wt % Al) film containing 8 wt % triflic acid and a commercial perfluorinated-sulfonic-acid polymer (Nafion® 117) film. At all three temperatures, proton conductivities are reduced in both materials at lower humidity levels, where dehydration effects are exacerbated. While Nafion® 117 retains higher conductivities close to saturated water conditions, the optimized mesostructured film exhibits substantially higher conductivities at low humidity levels. Furthermore, the optimized mesostructured film is significantly more stable, showing little change in proton conductivities measured across the temperature range 80-160° C. and across a broad humidity range.

More specifically, at 80° C. and relative humidities approaching 100%, Nafion® 117 was measured to have proton conductivity slightly above 0.1 S/cm [FIG. 7A]. Under these conditions, Nafion® 117 membranes typically display maximum proton conductivity performance. However, as also shown in FIG. 7A, as the relative humidity is decreased, the proton conductivity properties of Nafion® 117 rapidly diminish to values of $\sim 3 \times 10^{-3}$ S/cm at 20% RH. In contrast, the optimized PFSA-grafted aluminosilica film containing 8 wt % triflic acid backfilling the mesopores yields relatively constant proton conductivity values of $1-2 \times 10^{-2}$ S/cm over the range 40-100% RH (and maintains $5 \times 10^{-3}$ S/cm at 20% RH). Compared to Nafion® 117 at 80° C., the functionalized mesostructured film exhibits higher proton conductivity values at relative humidities below 30%. At higher temperatures, e.g., 120° C. [FIG. 7B] and 160° C. [FIG. 7C], the humidity at which this cross-over occurs increases, because at low relative humidities Nafion® 117 proton conductivity decreases significantly, while that for the PFSA-grafted aluminosilica film remains comparatively unchanged. In FIG. 7B, at 120° C., the PFSA-grafted aluminosilica film containing 8 wt % triflic acid shows higher conductivity values than Nafion® 117 for relative humidity values below 44%. At 160° C. [FIG. 7C], the humidity cross-over point is higher still, and the functionalized films exhibit higher conductivity values for relative humidities below 57% RH. Optimized surface compositions and structures in the multiply-functionalized mesostructured film thus yield attractive macroscopic properties that are comparable or superior to Nafion® 117 at low relative humidities (below ca. 50% RH) and higher temperatures (>120° C.).

Displaying the conductivity data as a function of temperature for the functionalized membranes in an Arrhenius-type plot allows the apparent activation energies for proton conduction to be determined. In particular, conductivity values at temperatures for the PFSA-aluminosilica films without and with 8 wt % triflic acid in FIG. 6C show Arrhenius-type behaviors below temperatures at which dehydration effects become significant (T≤120° C.) as seen in FIG. 13. Linear fits of the data yield apparent activation energies of 0.91 kJ/mol and 3.15 kJ/mol for the PFSA-aluminosilica membranes with and without triflic acid, respectively. The lower activation energy for proton transport in the triflic acid-containing membrane indicates that the highly mobile triflic acid species in the pores assist in proton transfer between grafted PFSA species. By comparison, Nafion® has been reported to have an apparent activation energy of 9.41 kJ/mol, which is almost three times higher than the acid-functionalized aluminosilica membrane without triflic acid and an order of magnitude higher than that of the optimally-functionalized PFSA-aluminosilica membrane containing 8 wt % triflic acid.

Finally, molecular interactions between adsorbed/grafted species and the heterogeneous framework affect not only the proton conductivity properties of the membranes, but also the thermal stabilities of the functional groups. Thermogravimetric analyses (TGA) conducted on the collectively optimized 5 wt % perfluorosulfonic-acid-grafted cubic mesoporous aluminosilica (3.5 wt % Al) films containing 8 wt % $F_3CSO_3H$ establish the relative and absolute thermal stabilities of adsorbed water and the acid functional species within the mesopores. Mass spectrometry measurements were conducted simultaneously on the effluent gases from the materials as they were heated to identify the chemical species responsible for specific mass losses as seen in FIG. 14. The TGA results seen in FIG. 8 show an initial 23% mass loss between room temperature and 220° C., which is attributed to adsorbed water within the mesopores. As established above by the $^{27}Al\{^1H\}$ HETCOR results in FIG. 4, a significant fraction of such water is strongly bound at six-coordinate $^{27}Al$ aluminosilica sites in the framework. The 8% mass loss between 225-325° C. results from triflic acid species that, despite their high relatively mobility, nevertheless are strongly interacting and retained in the mesopores, as established by the low-temperature $^{27}Al\{^{19}F\}$ and $^{29}Si\{^{19}F\}$ HETCOR results in FIG. 5. Interestingly, the combined TGA/mass spectrometry measurements in FIG. 14 also establish that the low-molecular-mass $F_3CSO_3H$ species decompose before desorbing from the mesopores. Samples with differences in triflic acid concentration back-filling the mesopores lead to expected differences in mass losses over the temperature range 225-325° C. Above 330° C., mass loss (3%) is caused by decomposition of covalently-grafted perfluorosulfonic acid species, with no further mass loss detected above 600° C. These macroscopic conductivity and thermal stability results are correlated and consistent with the collective molecular-level optimizations of functional group compositions and structures in the heterogeneous mesoporous aluminosilica films.

FIG. 9 through FIG. 14 provide a detailed mesostructural characterization by TEM, small-angle X-ray diffraction, and nitrogen sorption of the perfluorosulfonic acid grafted mesoporous aluminosilica membrane prior to backfilling of the mesopores with triflic acid. In addition, 2D $^{29}Si\{^{19}F\}$ HETCOR NMR spectrum acquired for a powder prepared from the perfluorosulfonic-acid-grafted cubic mesoporous aluminosilica film material prior to backfilling of the mesopores with triflic acid, showing unambiguous evidence of acid grafting to the aluminosilica surface through $^{19}F$-$^{29}Si$ heteronuclear dipole-dipole couplings.

Establishing the compositions, structures, distributions, and interfacial interactions of molecular species within multiply-functionalized mesoporous materials permits substantial control over their macroscopic properties, specifically with respect to temperature- and humidity-dependent proton conductivities of functionalized films. Furthermore, such insights yield important molecular design and processing criteria that allow the incorporation and collective optimization of several coupled properties, even those that may rely on incompatible synthesis conditions. The use of a sequential synthesis protocol overcomes previously severe limitations to the incorporation of technologically promising combinations of functional properties, which have previously not been possible to introduce together in a single set of synthesis-processing conditions. Two-dimensional heteronuclear chemical-shift correlation NMR spectroscopy has been used to characterize competitive molecular interactions in acid-functionalized mesoporous aluminosilica proton-exchange membrane materials. 2D $^{27}Al\{^{19}F\}$, $^{29}Si\{^{19}F\}$ and $^{27}Al\{^{1}H\}$ and $^{29}Si\{^{1}H\}$ HETCOR results establish unambiguously that perfluorosulfonic acid species are grafted to the mesopore surfaces preferentially through silica sites and that pore-filling water and triflic acid species interact strongly with both $^{29}Si$ and $^{27}Al$ surface sites. The combination of these results with complementary techniques, such as elemental analysis, quantitative single-pulse NMR, small-angle X-ray diffraction, and electron microscopy, provides a thorough understanding of the molecular and mesoscopic compositions and structures of these materials that are correlated with bulk material properties, such as proton conductivity and thermal stability. The insights provided by these results are expected to allow for extensive further optimization of the material compositions, and ultimately film/membrane performances in a variety of applications, particularly in fuel cells and batteries for which multi-functional materials may present significant new property advantages and device opportunities.

Example 2

In order to further demonstrate the functionality of the methods, an optimized, multiple-functional mesostructured material in a similar mesostructured silica system was produced in which mechanical and adsorption properties are separately adjusted. Porous materials often have properties that are dependent on heterogeneous internal interfaces that make them useful for a wide variety of technological applications, such as membrane separations, catalysts, fuel cells, batteries, etc. Recently, there has been significant interest in the incorporation of multiple functional properties into mesoporous and mesostructured materials and foams to combine several desirable properties into a single material. Such combinations properties, however, are often complicated to introduce, in part because they may involve separate and incompatible processing conditions or because they may be adversely coupled. Nevertheless, by careful control of synthesis conditions and steps, the compositions and structures of heterogeneous materials can be controlled to incorporate multiple functionalities and to optimize their properties for a variety of applications. For example, the compositions and structures of inorganic-organic hybrid materials can be adjusted to optimize their mechanical and adsorption properties for a range of applications, including foam barriers, fuel cell and battery membranes, catalysts and adsorbents.

By balancing the relative concentrations of networking-forming inorganic and organic components, we have recently synthesized mesoporous organosilica films, where mixed silica-resin wall networks were tuned independently of their mesopore surface compositions, thereby allowing independent control and optimization of mechanical and adsorption properties of the films.

The nanocomposites possessed a mesoscopically ordered silica framework that was interwoven with an organic resin component. In their syntheses, Pluronic® F127 poly(ethyleneoxide)-poly(propyleneoxide)-poly(ethyleneoxide) triblock copolymer species ($EO_{106}PO_{70}EO_{106}$), with ethyleneoxide (EO, —$OCH_2CH_2$—) and propyleneoxide (PO, —$OCH(CH_3)CH_2$—) monomer units, were used as the structure-directing agent in an ethanol solution with water as a cosolvent. Tetraethoxysilane [TEOS, $Si(OCH_2CH_3)_4$] were used as a network-forming inorganic precursor, and "resol" (an oligomeric compound formed by polymerization of phenol and formaldehyde) were used as a network-forming organic precursor. The procedure involved dissolving the F127 triblock copolymer in an acidic solution of ethanol and water, the subsequent addition of TEOS and resol into the same solution, mixing for 2 hours, and then casting into Petri dishes. The ethanol was allowed to evaporate for 5-8 hours at room temperature, after which the film was thermally polymerized at 100° C. for 24 hours to promote cross-linking of the resin species. After formation of the non-porous mesostructured composite films, the films were removed from their substrates, ground into a powder, and subsequently calcined at 350° C. for 3 hours under $N_2$ to remove the triblock copolymer species, but not the resin component within the silica framework. The powder was then carbonized at 900° C. for 2 hours under $N_2$ and the silica was subsequently removed via immersion in 10 wt % hydrofluoric acid for 24 hours to yield a mesoporous carbon powder product. Zhao and co-workers did not report the preparation of mesoporous silica-resin films, nor did they report mechanical property measurements of any kind. The mechanical implications of incorporating an organic resin component within the silica framework were not discussed, nor optimization or correlations or with other material properties. No data or results were presented to correlate mechanical properties of the materials with the organic resin composition of the frameworks, with compositions of the mesopore surface or inorganic-organic interfaces, or extent of resin polymerization.

Porous organosilica materials have been prepared as films, whose mechanical, adsorption, and transport properties are adjustable and optimizable, according to their framework compositions and pore sizes, surface compositions, and structures. In particular, the mechanical properties can be adjusted by changing the relative fractions and extents of polymerization of network-forming inorganic (e.g., silica) and organic (e.g., resin) components in the mesoporous frameworks. Moreover, the compositions of the resulting framework can be controlled without significantly affecting the pore surfaces, thus allowing independent control of the bulk mechanical and adsorption/reaction properties of the material. The ability to separately tune and optimize these important materials properties is novel, general, and dramatically increases the versatility of these materials, which can be functionalized for specific barrier, membrane, catalyst, or device applications.

The mesoporous organosilica films were synthesized by a combination of sol-gel chemistry, evaporation-induced self-assembly of block-copolymer species from solution, and in-situ polymerization of organic precursors. A schematic diagram of the synthesis protocol is shown in FIG. 15A. A Pluronic® F127 mesostructure-directing species, hydrolyzed TEOS, resin-forming resorcinol and formaldehyde, and ethanol and water solvents were used. The F127 triblock copolymer species were dissolved and the TEOS hydrolyzed under acidic conditions in separate solutions for 45 min before being combined into one solution. The organic resorcinol-formaldehyde monomers (rather than pre-polymerized phenol-formaldehyde oligomers) were then added to this combined solution and stirred for 2 hours. Afterwards, the solution was cast into a Petri dish, and the ethanol was allowed to evaporate for 1-7 days to reduce drying stresses before thermal polymerization of the network-forming organic species. As the solvents evaporate, the components self-assemble as directed by the F127 species, and a film forms with a thickness that depends upon the depth of the solution in the dish, the rate of solvent removal, and the solution viscosity. This is accompanied by condensation of the silica species, with the resorcinol-formaldehyde (resin precursor) species interspersed within the silica network. The resorcinol-formaldehyde species are then thermally polymerized at 100° C. to form a resinous component within the silica framework; the rates of heating/cooling and duration of heat treatment influence the degree of polymerization of the resorcinol-formaldehyde resin and thus allow the mechanical properties of the film to be adjusted. The resulting films have cubic mesostructural order with interconnecting channels formed by interspersed silica-resin networks, as illustrated in FIG. 15B.

Powerful solid-state one-dimensional (1D) and two-dimensional (2D) $^1$H, $^{13}$C, and $^{29}$Si nuclear magnetic resonance (NMR) spectroscopy techniques are being applied to gain molecular-level insights on mesostructured silica-resin material compositions, structures, dynamics, and interfaces. These techniques permit quantitative understanding, control, and optimization of organic resin content and extent of resin polymerization, as well as how they may affect the bulk mechanical, adsorption, and transport/permeability properties of the materials. A $^{13}$C cross polarization of magic-angle-spinning (CP-MAS) NMR spectrum, along with corresponding peak assignments, are shown in FIG. 16 for a powder sample prepared from a cubic mesostructured silica-resin film containing an initial organic precursor/TEOS ratio of 0.20 and thermally polymerized at 100° C. for 12 hours. The $^{13}$C signals that are labeled '1'-'9' correspond to moieties that are associated with the cross-linked resorcinol-formaldehyde resin. The $^{13}$C signal labeled '10' corresponds to a hydroxymethyl product of the reaction between resorcinol and formaldehyde, two of which can react to form a dimethylene-ether cross-link that in turn dissociates to form a methylene cross-link between the aryl rings (with formaldehyde as a byproduct). The $^{13}$C signals labeled '11'-'13' correspond to the different moieties of the structure-directing triblock copolymer F127 species present within the mesochannels. In particular, the $^{13}$C peaks labeled '7' and '9' provide direct molecular evidence of cross-linking methylene groups that form the bridges between the aryl rings of the resin.

While the $^{13}$C CP-MAS NMR spectrum provides enhanced signal sensitivity, a single-pulse $^{13}$C spectrum will be acquired and from which the integrated $^{13}$C signals will be used to quantify the amount of organic resin and its extent of cross-linking in the materials. The pore surfaces and pore volumes of these materials will be functionalized to impart desired additional functionalities (e.g., hydrophilicity, hydrophobicity, ion-conduction, etc.), which will be characterized and optimized by using solid-state two-dimensional $^{13}$C{$^1$H} NMR and correlated with macroscopic material properties. In combination, these measurements will establish the nature and extent of resin cross-linking and interfacial compositions and structures within the inorganic frameworks and at pore surfaces within these complex materials. The molecular level insights will provide important feedback for understanding and optimizing the effect(s) that resin content and polymerization have on the bulk properties of different functionalized materials.

The mechanical properties of the silica-resin films are particularly important to understand and control. They are influenced greatly by the relative resin/silica contents and the extent of polymerization of the organic resin, both of which are adjustable. For example, nano-indentation measurements show that film properties can be varied from hard and brittle for high extents of resin polymerization, to more elastic for lower extents of polymerization across a range of resin concentrations.

Table 2 summarizes the mechanical properties of cubic mesoporous silica films and cubic mesoporous silica-resin films measured by using a Hysitron® nanoindenter. These measurements show that a cubic mesostructured F127-silica-resin film possesses a Young's modulus that is lower than that of a cubic mesostructured F127-silica films (without the resin component). In addition, a cubic mesoporous silica-resin film (after extraction of the F127 triblock-copolymer species) possesses a much lower hardness value that that of conventional cubic mesoporous silica films (without resin or F127). A lower Young's modulus generally corresponds to materials that are more elastic and mechanically flexible. These results establish that the incorporation of organic resin into the mesostructured silica materials can directly and beneficially affect the mechanical properties of films by imparting greater flexibility. Furthermore, because the resin network is interspersed within the silica (or other inorganic) framework, the mechanical properties of these mesostructured materials can be adjusted independently of separate functionalization of their interior or exterior pore surfaces or volumes.

The selection of resorcinol and formaldehyde organic precursors and the accompanying acidic synthesis conditions favor the formation of linear resin chains upon thermal polymerization. Furthermore, relatively low concentrations of linear resin oligomers or polymers interspersed within the silica network allow control over the mechanical properties of the resulting silica-resin films without altering the film mesostructural ordering or, importantly, mesopore surface compositions. These material and chemical modifications represent key differences, in addition to the specific synthesis differences highlighted above, from the material compositions and objections of Zhao et al., which were based upon high contents of phenol-formaldehyde resin under synthesis conditions that favored the formation of 3D organic networks. The capability to optimize separately and collectively the bulk mechanical, adsorption, and/or other properties is desirable for numerous applications, notably in films or membranes. Technologically important examples are for fuel cells or batteries, where brittle films may otherwise be prone to cracking when hot pressed into membrane electrode assemblies and where adsorption and/or ion-properties must be maintained.

From the foregoing it can be seen that the present invention can be embodied in various ways, including, but not limited to, the following:

1. A method for producing a multiply functionalized mesostructured material, the method comprising providing a mesostructured material; performing a first processing step to introduce a first functional property into a mesostructured material under a first set of process conditions; and performing a second processing step to introduce a second functional property into the mesostructured material under a second set of process conditions, the second set of process conditions being different from the first set of process conditions.

2. The method of embodiment 1, further comprising: performing a third processing step to introduce a third functional property into the mesostructured material under a third set of process conditions, the third set of process conditions being different from the first set and second set of process conditions.

3. The method of embodiment 1, further comprising: independently adjusting the first processing conditions and the second processing conditions to control the first functional property and the second functional property.

4. The method of embodiment 1: wherein the first processing step provides a first functional agent and the second processing step provides a second functional agent; wherein the first and second functional agents are identical; wherein the first processing step and the second processing step are different; and wherein the functional property introduced by the first processing step is different from the functional property introduced by the second processing step.

5. The method of embodiment 1, further comprising: functionalizing the mesostructured material with one or more functional agents that are disposed within pores or channels of the mesostructured material.

6. The method of embodiment 5, wherein the functional agent is an optically responsive organic species selected from the group of agents consisting essential of dyes, porphyrins, or conjugated polymers.

7. The method of embodiment 5, wherein the functional agents are semiconducting nanoparticles selected from the group of nanoparticles consisting essentially of ZnSe, ZnS, CdSe, CdS, GaN, GaP, InP, InGaP, GaAs, AlGaAs, or their oxides.

8. The method of embodiment 1: wherein the mesostructured material comprises a silica or organosilica framework; wherein the first functional property comprises hydrophilic aluminosilica moieties; and wherein the second functional property comprises acid groups.

9. The method of embodiment 2, wherein the first set of processing conditions are acidic conditions, the second set of processing conditions are alkaline conditions, and the third set of processing conditions are non-aqueous conditions.

10. A method of forming a multiply functionalized mesostructured material, the method comprising: creating a mesostructural material with a network that is removed to yield a mesoporous material; performing a first processing step to introduce a first functional property into the mesoporous material under a first set of process conditions; performing a second processing step to introduce a second functional property into the mesoporous material under a second set of process conditions, the second set of process conditions being different from the first set of process conditions; and performing one or more additional processing steps to introduce additional functional properties into the mesoporous material under additional sets of process conditions, the additional sets of process conditions being different from the first or immediately preceding sets of process conditions.

11. The method of embodiment 10, wherein the functionalities are selected from the group of functionalities consisting essentially of hydrophilicity, hydrophobicity, ion-conduction, adsorption selectivity, chemical reactivity, transport, electrical conduction, mechanical, optical, or opto-electronic properties.

12. The method of embodiment 10, wherein the network that is removed to yield a mesoporous material is formed with a material selected from the group of materials consisting essentially of a surfactant, a polymer, a block-copolymer, epoxy, resorcinol, phenol, an organometallic compound, or a dye.

13. The method of embodiment 12, wherein the selected material is incorporated over a range of 0-50 weight percentage to adjust the mechanical, optical, opto-electronic, adsorption, transport, or reaction properties of the mesostructured material.

14. The method of embodiment 10, wherein the first functional property comprises aluminum-containing moieties, the aluminum-containing moieties occupying surface sites to enhance the hydrophilicity or reaction properties of the mesoporous material.

15. A multiply functionalized mesostructured material comprising a first functional agent that provides a first functional property, a second functional agent that provides a second functional property, and optionally additional functional agents provide additional functional properties, wherein the multiply functionalized mesostructured material is prepared by a process comprising: performing a first processing step to introduce a first functional property into a mesostructured material under a first set of process conditions; performing a second processing step to introduce a second functional property into the mesostructured material under a second set of process conditions, the second set of process conditions being different from the first set of process conditions; and optionally performing additional processing steps to introduce one or more additional functional properties into the mesostructured material under additional sets of process conditions, the additional sets of process conditions being different from the first or immediately preceding sets of process conditions.

16. The multiply functionalized mesostructured material as recited in embodiment 15, wherein the first functional property, the second functional property, and optionally additional functional properties are independently selected from the group of properties consisting essentially of hydrophilicity, hydrophobicity, ion-conduction, adsorption selectivity, chemical reactivity, transport, electrical conduction, mechanical, optical, or opto-electronic properties.

17. The multiply functionalized mesostructured material of embodiment 15, wherein the first processing step and the second processing step are different, and wherein the first and second functional properties are different.

18. The multiply functionalized mesostructured material as recited in embodiment 15, further comprising: one or more functional agents disposed within pores of the mesostructured material, the functional agent comprising a nanoparticle.

19. The multiply functionalized mesostructured material as recited in embodiment 18, wherein said functional agent nanoparticles are semiconducting nanoparticles selected from the group of nanoparticles consisting essentially of ZnSe, ZnS, CdSe, CdS, GaN, GaP, InP, InGaP, GaAs, AlGaAs, or their oxides.

20. The multiply functionalized mesostructured material as recited in embodiment 18, further comprising: one or more functional agents disposed within pores of said mesostructured material, the functional agent selected from the group of functional agents consisting essentially of a dye, a porphyrin, or a conjugated polymer.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

| Functionalized cubic mesoporous films | Elemental Analysis | | 1-Pulse $^{27}$Al MAS NMR | |
|---|---|---|---|---|
| | Si/Al molar ratio | wt % Al | $Al^{IV}$ (%) | $Al^{VI}$ (%) |
| silica | ∞ | 0 | — | — |
| aluminosilica | 15.6 ± 0.5 | 3.7 | 92 | 8 |
| PFSA-aluminosilica | 16.8 ± 0.4 | 3.5 | 39 | 61 |
| PFSA-aluminosilica with 8 wt % CF$_3$SO$_3$H | 16.9 ± 0.2 | 3.5 | 1 | 99 |

TABLE 2

| Sample | Young's Modulus (GPa) | Hardness (GPa) |
|---|---|---|
| As-synthesized cubic mesostructured F127-silica film | 0.541 ± 0.008 | 0.110 ± 0.002 |
| Cubic mesoporous silica film (calcined, F127 triblock copolymer removed) | 7.27 ± 0.4 | 3.8 ± 0.1 |
| As-synthesized cubic mesostructured F127-silica-resin film | 0.435 ± 0.002 | 0.112 ± 0.002 |
| Cubic mesoporous silica-resin film (solvent-extracted, F127 triblock copolymer removed) | 4.43 ± 0.1 | 0.742 ± 0.003 |

What is claimed is:

1. A sequential method of forming a multiply functionalized mesostructured material, the method comprising:
    providing a mesostructured material with a characteristic porosity;
    grafting species containing metal atoms on surfaces of pores of the mesostructured material;
    incorporating molecules on surfaces of pores of the mesostructured material that have at least one acidic or basic functional group; and
    adsorbing functional agents into pore spaces of said mesostructured material;
    wherein said functional agents are semiconducting nanoparticles selected from the group of nanoparticles consisting of ZnSe, ZnS, CdSe, CdS, GaN, GaP, InP, InGaP, GaAs, AlGaAs, and their oxides.

2. The method as recited in claim 1, further comprising: providing a microporous mesostructured material with interconnecting microchannels between pores or channels of the mesostructured material.

3. The method as recited in claim 1:
    wherein the mesostructured material comprises a silica or organosilica framework;
    wherein the grafted metal species comprises hydrophilic aluminosilica moieties; and
    wherein the incorporated surface molecules comprises triflic acid molecules.

4. A method of forming a multiply functionalized mesostructured material, the method comprising:
    creating a mesostructural material with a network that is removed to yield a mesoporous material;
    performing a first processing step to introduce a first functional property into the mesoporous material under a first set of process conditions;
    performing a second processing step to introduce a second functional property into the mesoporous material under a second set of process conditions, the second set of process conditions being different from the first set of process conditions;
    performing a third processing step to introduce a third functional property on to surfaces of the mesoporous material under a third set of process conditions, the third set of process conditions being different from the first set and second set of process conditions; and
    depositing nanoparticles of one or more functional agents within pores of the mesostructured material;
    wherein said functional agents are semiconducting nanoparticles selected from the group of nanoparticles consisting of ZnSe, ZnS, CdSe, CdS, GaN, GaP, InP, InGaP, GaAs, AlGaAs, and their oxides.

5. The method as recited in claim 4, wherein said functionalities are selected from the group of functionalities consisting of hydrophilicity, hydrophobicity, ion-conduction, adsorption selectivity, chemical reactivity, transport, electrical conduction, mechanical, optical, and opto-electronic properties.

6. The method as recited in claim 4, wherein said network that is removed to yield a mesoporous material is formed with a material selected from the group of materials consisting of a surfactant, a polymer, a block-copolymer, epoxy, resorcinol, phenol, an organometallic compound, and a dye.

7. The method of claim 6, wherein said selected material is incorporated over a range of 0-50 weight percentage to adjust the mechanical, optical, opto-electronic, adsorption, transport, or reaction properties of the mesostructured material.

8. The method of claim 4, wherein said first functional property comprises aluminum-containing moieties, said aluminum-containing moieties occupying surface sites to enhance the hydrophilicity and reaction properties of the mesoporous material.

* * * * *